US012215334B2

(12) United States Patent
Kusano et al.

(10) Patent No.: US 12,215,334 B2
(45) Date of Patent: Feb. 4, 2025

(54) POLYNUCLEOTIDE FOR MODIFYING TARGET SEQUENCE AND USE THEREOF

(71) Applicant: I'ROM GROUP CO., LTD., Tokyo (JP)

(72) Inventors: Kohji Kusano, Tokyo (JP); Takayuki Kitogo, Tokyo (JP); Makoto Inoue, Tokyo (JP); Tsugumine Shu, Tokyo (JP); Toyotaka Mori, Tokyo (JP)

(73) Assignee: I'ROM GROUP CO., LTD., Tokyo (JP)

( * ) Notice: Subject to any disclaimer, the term of this patent is extended or adjusted under 35 U.S.C. 154(b) by 1329 days.

(21) Appl. No.: 16/631,407

(22) PCT Filed: Jul. 19, 2018

(86) PCT No.: PCT/JP2018/027141
§ 371 (c)(1),
(2) Date: Jan. 15, 2020

(87) PCT Pub. No.: WO2019/017438
PCT Pub. Date: Jan. 24, 2019

(65) Prior Publication Data
US 2020/0216858 A1 Jul. 9, 2020

(30) Foreign Application Priority Data
Jul. 21, 2017 (JP) ................. 2017-141691

(51) Int. Cl.
| | | |
|---|---|---|
| C12N 15/11 | (2006.01) | |
| A61K 39/155 | (2006.01) | |
| C12N 7/00 | (2006.01) | |
| C12N 15/00 | (2006.01) | |
| C12N 15/85 | (2006.01) | |
| C12N 15/86 | (2006.01) | |

(52) U.S. Cl.
CPC ............ *C12N 15/85* (2013.01); *A61K 39/155* (2013.01); *C12N 7/00* (2013.01); *C12N 15/00* (2013.01); *C12N 15/11* (2013.01); *C12N 15/86* (2013.01); *C12N 2320/00* (2013.01); *C12N 2710/16643* (2013.01); *C12N 2760/18011* (2013.01); *C12N 2760/18842* (2013.01); *C12N 2800/10* (2013.01); *C12N 2810/6072* (2013.01)

(58) Field of Classification Search
CPC .. C12N 2310/20; C12N 15/63; C12N 15/102; C12N 15/11; C12N 2800/80; C12N 2800/30; C12N 15/111; C12N 15/67; C12N 15/902; C12N 15/90; C12N 15/8213; C12N 15/1082; C12N 15/87; C12N 15/86; C12N 2510/00
See application file for complete search history.

(56) References Cited

U.S. PATENT DOCUMENTS

| | | |
|---|---|---|
| 7,285,699 B2 | 10/2007 | Golic |
| 2004/0068761 A1 | 4/2004 | Golic et al. |
| 2013/0263292 A1* | 10/2013 | Liang ................. C12N 15/8509 435/328 |

FOREIGN PATENT DOCUMENTS

| | | |
|---|---|---|
| EP | 1 179 594 | 2/2002 |
| EP | 1642966 | 4/2006 |
| EP | 2048232 | 4/2009 |
| JP | 2018126122 A * | 8/2018 |
| WO | WO- 2000/070055 | 11/2000 |
| WO | WO2014/199358 | 12/2014 |
| WO | WO2015/095804 | 6/2015 |

OTHER PUBLICATIONS

Takehara et al., A novel transchromosomic system: stable maintenance of an engineered Mb-sized human genomic fragment translocated to a mouse chromosome terminal region, Transgenic Research, vol. 23, pp. 441-453. (Year: 2014).*
Manivannan et al., Targeted integration of single-copy transgenes in *Drosophila melanogaster* tissue-culture cells using recombination-mediated cassette exchange, Genetics, volme 201, pp. 1319-1328. (Year: 2015).*
Wu et al., Double replacement: Strategy for efficient introduction of subtle mutations into the murine col. 1a-1 gene by homologous recombination in embryonic stem cells, PNAS, vol. 91, pp. 2819-2823. (Year: 1994).*
Bitzer et al., "Sendai virus vectors as an emerging negative-strand RNA viral vector system," J Gene Med (2003) 5(7):543-553.
Fusaki et al., "Efficient induction of transgene-free human pluripotent stem cells using a vector based on Sendai virus, an RNA virus that does not integrate into the host genome," Proc Jpn Acad Ser B Phys Biol Sci (2009) 85(8):348-362.
De Piedoue et al., "Improving gene replacement by intracellular formation of linear homologous DNA," J Gene Med (2005) 7(5):649-656.
Xie et al., "Gene Deletions by Ends-In Targeting in *Drosophila melanogaster*," Genetics (2004) 168(3):1477-1489.
Mansour et al., "Disruption of the proto-oncogene int-2 in mouse embryo-derived stem cells: a general strategy for targeting mutations to non-selectable genes," Nature (1988) 336(6297):348-352.
Morton et al., "Induction and repair of zinc-finger nuclease-targeted double-strand breaks in *Caenorhabditis elegans* somatic cells," PNAS USA (2006) 103(44):16370-16375.

(Continued)

*Primary Examiner* — Dana H Shin
(74) *Attorney, Agent, or Firm* — MORRISON & FOERSTER LLP

(57) ABSTRACT

The present invention provides donor polynucleotides formed by linking the two ends of a genomic fragment containing a cleavable site by a polynucleotide carrying a positive selection marker gene and a negative selection marker gene. Use of the donor polynucleotide makes it possible to modify only a target gene with avoiding the possibility of introducing mutations to sequences, called "off-target", which are other than the target sequence, by introducing cleavage in a homologous site of the donor polynucleotide without introducing cleavage in a target gene locus.

10 Claims, 5 Drawing Sheets

Specification includes a Sequence Listing.

(56) References Cited

OTHER PUBLICATIONS

Cermak et al., "Efficient design and assembly of custom TALEN and other TAL effector-based constructs for DNA targeting," Nucleic Acids Res (2011) 39(12):e82.
Cong et al., "Multiplex genome engineering using CRISPR/Cas systems," Science (2013) 339(6121):819-823.
International Search Report for PCT/JP2018/027141, dated Oct. 23, 2018, 2 pages.
International Preliminary Report on Patentability for PCT/JP2018/027141, dated Oct. 23, 2018, 6 pages.
Mali et al., "RNA-guided human genome engineering via Cas9," Science (2013) 339(6121):823-826.
Li et al., "Precise Correction of the Dystrophin Gene in Duchenne Muscular Dystrophy Patient Induced Pluripotent Stem Cells by TALEN and CRISPR-Cas9," Stem Cell Reports (2015) 4(1):143-154.
Yusa et al., "Targeted gene correction of α1-antitrypsin deficiency in induced pluripotent stem cells," Nature (2011) 478(7369):391-394.

\* cited by examiner

POLYNUCLEOTIDE FOR MODIFYING TARGET SEQUENCE AND USE THEREOF

CROSS-REFERENCE TO RELATED APPLICATIONS

This application is the national phase of PCT application PCT/JP2018/027141 having an international filing date of Jul. 19, 2018, which claims benefit of Japanese patent application No. 2017-141691 filed Jul. 21, 2017. The contents of the above patent applications are incorporated by reference herein in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 532842001400SUBSEQLIST.txt, date recorded: Dec. 5, 2024, size: 14,607 bytes).

TECHNICAL FIELD

The present invention relates to molecular genetic techniques for precisely modifying a gene sequence for the purpose of gene therapy, breed improvement, biotechnological creation, and such.

BACKGROUND ART

The ZFN method, TALEN method, and CRISPR/Cas9 method are known as techniques for improving gene modification frequency by cleaving a target site of a genomic nucleotide sequence for the purpose of genetic modification (Morton, J., et al., Proc. Natl. Acad. Sci. USA 103, 16370-16375 (2006); Cermak, T. et al., Nucleic Acids Res. 39, e82 (2011); Cong, L. et al., Science 339, 819-823 (2013); and Mali, P. et al., Science 339, 823-826 (2013)).

However, even though trying to introduce a donor DNA having a modified nucleotide sequence and to modify a target site by any one of the three methods mentioned above, it is not easy to obtain cells in which the target site is accurately converted to the modified nucleotide sequence desired to be introduced while any other modification is not contained.

For example, in the ZFN method, TALEN method, and CRISPR/Cas9 method, it is difficult to very strictly control the target sequence specificity, and off-target sequences similar to the target sequence may be cleaved, thus generating insertions or deletions called indel during rejoining (inaccurate rejoining) (problem of off-target inaccurate rejoining). Furthermore, even when the target sequence is cleaved, introduction of indel during rejoining is a remaining concern (problem of on-target inaccurate rejoining). However, such phenomena must be avoided in the case of precise genetic modification such as in gene therapy.

For selection of cells having the modified sequence of interest introduced into its genome, a drug selection marker gene is generally used. In a conventional method, a vector is constructed to have the marker gene inserted into the nucleotide sequence of an intron neighboring the exon nucleotide sequence to be modified, the vector is introduced into cells, and after inducing homologous recombination, drug selection is carried out. However, since the obtained cells of course have the marker gene, unless some measures are taken, the marker gene will remain in the nucleotide sequence of the intron integrated into the genome of the cells.

In order to remove this marker gene, a donor DNA is used, in which a drug resistance marker gene sandwiched between the sequences recognized by a site-specific recombinase (LoxP or FRT) has been inserted into the intron proximate to the exonic modified nucleotide sequence of interest. The donor DNA is introduced into cells, the exon-intron region is cleaved, cell clones having integrated into its genome a long chain starting from the intronic drug resistance marker gene to the exonic modified nucleotide sequence are isolated, then the site-specific recombinase (Cre or Flp) gene is introduced into the cell clones to obtain cells from which only the drug resistance marker is lost (Li, H. L. et al., Stem Cell Reports 4, 143-154 (2015)).

This method removes only the selection marker gene sandwiched between the sequences recognized by site-specific recombinases (LoxP and FRT) through site-specific recombination; meanwhile, such methods represented by the Cre/LoxP method and the Flp/FRT method cause one recognition sequence to remain without being removed due to the characteristic of the recombinases, which leads to the problem of not being applicable to gene therapy or precise genetic modifications (problem of residual site-specific recombination sequence).

Furthermore, this method involves a complicated procedure such that it requires, after selecting the donor DNA introduced cells, an additional step of introducing a vector which expresses a site-specific recombinase or such into the cells, and additionally requires confirmation of removal of the introduced site-specific recombinase expression vector from the cells.

Another method uses a donor DNA produced by inserting a drug resistance marker gene sandwiched between the sequences recognized by a transposase (PiggyBac ITR) into the intron proximate to the exonic modified nucleotide sequence of interest. The donor DNA is introduced into cells, the exon-intron region is cleaved, cell clones having integrated into its genome a long chain starting from the intronic drug resistance marker gene to the exonic modified nucleotide sequence are isolated, then the transposase (PiggyBac transposase) gene is introduced into the cell clones to obtain cells from which the drug resistance marker and the recognition sequence (PiggyBac ITR) are lost (Yusa, K. et al., Nature 478, 391-394 (2012)).

However, this method has two problems. One is that the position for inserting the selection marker gene sandwiched between PiggyBac ITR is limited to the TTAA sequence. In other words, unless a TTAA sequence exists near the site to be modified, the method cannot be applied. The other problem is that even if the method could be applied, the procedure becomes complicated such that it requires, after selecting the donor DNA-introduced cells, an additional step of introducing a vector that expresses transposase or such into the cells, and further requires confirmation of removal of the introduced transposase expression vector from the cells.

As described above, in the methods using ZFN, TALEN, and CRISPR/Cas9, the genomic target site of the cells subjected to genome editing is specifically cleaved, and at this site, homologous recombination with the target sequence in the donor plasmid takes place. In methods dependent on this mechanism, homologous recombination reaction is inhibited when the donor plasmid-derived target sequence is cleaved in addition to the target sequence on the chromosomal gene locus; therefore, cleavage of the donor plasmid-derived target sequence must be avoided by removing the target nucleotide sequence on the donor plasmid (or converting this sequence to a nontargeted sequence). However, if the donor DNA sequence is modified for this purpose, cells having the modified sequence integrated into their genome will lose the original genomic sequence from this region, which leads to the problem of not being applicable to gene therapy or precise genetic modification (problem of genomic sequence loss at the cleavage site).

CITATION LIST

Non-Patent Literature

[NPL 1] Morton, J., Davis, M. W., Jorgensen, E. M. & Carroll, D. Induction and repair of zinc-finger nuclease-targeted double-strand breaks in Caenorhabditis elegans somatic cells. Proc. Natl. Acad. Sci. USA 103, 16370-16375 (2006)
[NPL 2] Cermak, T. et al. Efficient design and assembly of custom TALEN and other TAL effector-based constructs for DNA targeting. Nucleic Acids Res. 39, e82 (2011)
[NPL 3] Cong, L. et al. Multiplex genome engineering using CRISPR/Cas systems. Science 339, 819-823 (2013)
[NPL 4] Mali, P. et al. RNA-guided human genome engineering via Cas9. Science 339, 823-826 (2013)
[NPL 5] Li, H. L. et al. Precise Correction of the Dystrophin Gene in Duchenne Muscular Dystrophy Patient Induced Pluripotent Stem Cells by TALEN and CRISPR-Cas9. Stem Cell Reports 4, 143-154 (2015)
[NPL 6] Yusa, K. et al. Targeted gene correction of a1-antitrypsin deficiency in induced pluripotent stem cells. Nature 478, 391-394 (2012)

SUMMARY OF THE INVENTION

Technical Problem

The present invention relates to donor polynucleotides for efficiently modifying genomic sequences, methods for producing genome-modified cells using the donor polynucleotides, and such.

Solution to Problem

On/Off-Target Inaccurate Rejoining

As described above, since the enzymes currently used in genome editing cleave target sequences on the chromosome, there are concerns regarding risks of off-target cleavage where chromosome sites other than the target are cleaved, and risks of indel introduction when the cleaved genome is repaired. To avoid these problems, the present inventors arrived at the idea of cleaving only the donor plasmid and not the chromosome. For example, if the homologous region in the donor plasmid, which contains the post-modification sequence, is cleaved before introduction and the resulting linear donor plasmid is introduced into cells, or if a circular donor plasmid is introduced into cells and the donor plasmid is cleaved sequence-specifically in the cells, the target sequence or the off-target sequence similar to the target sequence (On/Off-Target) will not be cleaved. Accordingly, inaccurate rejoining will not take place and indel will not be introduced, and this idea will become a technique suitable for precise genetic modification such as gene therapy.

Residual Site-Specific Recombination Site

Furthermore, to introduce only the necessary modifications to the target site in genome editing, and to avoid leaving behind the marker gene or marks of removing the marker gene, the present inventors arrived at the idea of positioning both a positive selection marker gene and a negative selection marker gene at the outside of the genomic fragment in the donor plasmid. In this case, since two selection marker genes are positioned in the donor plasmid framework, the entire donor plasmid is inserted by homologous recombination that takes place in the target sequence region to thereby form a vector-inserted target construct, in which the post-modification nucleotide sequence from the donor plasmid and the pre-modification nucleotide sequence on the chromosome (in no particular order) are arranged in tandem, with the framework region of the donor plasmid being sandwiched between the two sequences. The post-modification nucleotide sequence and the pre-modification nucleotide sequence included in this intermediate structure readily undergo homologous recombination. Because of this, by simply culturing cells carrying this structure in their genome, this structure will be spontaneously replaced with a single structure having only the post-modification nucleotide sequence. This process does not require site-specific recombinases, transposase, or such, thus makes it possible to obtain cells of interest very easily. This process is also superior in providing no possibility of leaving behind a specific recombination recognition sequence.

Loss of Target Cleavage Sequence

As described above, when not only the target sequence on the chromosomal gene locus but also the donor plasmid-derived target sequence is cleaved, homologous recombination reaction between the long chain region on the donor plasmid and the target site on the gene locus is inhibited. In a conventional method, cleavage of the homologous region on the donor plasmid side is avoided by removing the cleavage sequence from the donor plasmid; however, such a method causes concerns that the modified sequence in which the cleavage sequence has been removed will become integrated into the chromosome of the cells. In contrast, in an embodiment of the present invention, the homologous region in the donor plasmid, which contains the post-modification sequence, is cleaved before introduction and the resulting linear donor plasmid is introduced to thereby avoid cleavage of both the target sequence on the chromosomal gene locus and the donor plasmid-derived target sequence. Furthermore, in another embodiment of the present invention, a recognition sequence of a sequence-specific cleavage enzyme represented by, for example, I-SceI, is inserted to a genomic fragment in a donor plasmid, the sequence-specific cleavage enzyme gene is allowed to be expressed inside the cells prior to, subsequent to, or simultaneously with introduction of the donor plasmid into the cells, and the recognition sequence in the donor plasmid is cleaved. The recognition sequence of the sequence-specific cleavage enzyme is not present in the corresponding region on the gene locus of the chromosome of the cells; therefore, it becomes possible to avoid cleavage of both the target sequence on the chromosomal gene locus and the donor plasmid-derived sequence and to prevent a decrease in efficiency of homologous recombination.

As noted above, the present invention provides new genome editing techniques that solve the problems of conventional genome editing techniques. Such techniques allow easy and accurate introduction of only the modifications of interest into the genome.

That is, the present invention relates to novel donor polynucleotides for modifying genomic sequences and uses thereof, and more specifically, it relates to the invention set forth in each of the claims. Inventions comprising any combination of two or more inventions set forth in the claims that refer to the same claim are also inventions intended in this description. More specifically, the present invention relates to the following.

[1] A donor polynucleotide for modifying a genomic sequence, wherein the donor polynucleotide comprises a genomic fragment comprising one or more modifications, wherein both ends of the genomic fragment are linked by a polynucleotide, wherein the linker polynucleotide comprises within it both a positive selection marker gene and a negative selection marker gene, wherein the genomic fragment is cleavable, and wherein the donor polynucleotide may be linear when the cleavable site is severed to become the two ends of the donor polynucleotide chain, or the donor polynucleotide may be circular when the site is connected in the donor polynucleotide.

[2] The donor polynucleotide of [1], wherein a cleavage sequence is added to the cleavable site.

[3] The donor polynucleotide of [2], wherein the cleavage sequence added to the site is not contained in a sequence of a target cell genomic fragment corresponding to the genomic fragment comprised in the donor polynucleotide.

[4] The donor polynucleotide of any one of [1] to [3], wherein in the genomic fragment, the one or more modifications are included only on one side of the site.

[5] The donor polynucleotide of any one of [1] to [4], wherein the linker polynucleotide is a polynucleotide of a plasmid.

[6] The donor polynucleotide of any one of [1] to [5], which does not comprise a target cell genomic sequence in between the positive selection marker gene and the negative selection marker gene.

[7] The donor polynucleotide of any one of [1] to [6], wherein the positive selection marker gene and the negative selection marker gene are fused, and the positive selection marker and the negative selection marker are expressed as a fusion protein.

[8] A method for modifying a genomic sequence, which comprises the steps of: (a) introducing the donor polynucleotide of any one of [1] to [7] into cells; (b) selecting, using a positive selection marker, cells into which the donor polynucleotide has been introduced; and (c) selecting, using a negative selection marker, cells in which the linker polynucleotide has been removed.

[9] The method of [8], wherein step (a) comprises a step of introducing into cells a linear donor polynucleotide formed by severing the site of the donor polynucleotide

[10] The method of [8], wherein step (a) comprises a step of introducing into cells a circular donor polynucleotide, in which the site is connected, and a cleavage enzyme that cleaves the site or a vector that expresses the enzyme.

[11] The method of [10], which comprises introducing the circular donor polynucleotide simultaneously with the enzyme or the vector.

[12] The method of or [11], wherein the vector that expresses the enzyme is a minus strand RNA virus vector that expresses the enzyme.

[13] The method of any one of [8] to [12], which further comprises a step of selecting a cell comprising a modification of interest in its genome.

[14] The method of any one of [8] to [13], which is used to convert a disease-causing sequence to a normal sequence in a causative gene of a hereditary disease.

[15] A cell having a structure in which the donor polynucleotide of any one of [1] to [7] has been incorporated into its genome, wherein the modified genomic fragment included in the donor polynucleotide and a fragment corresponding thereto derived from the genome of the cell have a structure in which they are arranged in tandem in no particular order via the linker polynucleotide, and wherein the linker polynucleotide comprises within it a positive selection marker gene and a negative selection marker gene.

[16] A method for producing a cell with a modified genome, which comprises a step of subjecting the cell of to selection using a negative selection marker to select cells in which the linker polynucleotide has been removed.

[17] A minus strand RNA virus vector for use in the method of [12], which encodes an endonuclease that cleaves the cleavage site of the donor polynucleotide.

[18] The vector of [17], which is a Sendai virus vector.

[19] The vector of or [18], wherein the endonuclease is I-SceI.

[20] A composition for use in the method of [12], which comprises the vector of any one of to [19].

It is intended that any technical matters described herein, and any combinations thereof are included herein. In addition, it is intended that in the present invention, inventions excluding any matters described herein or any combinations thereof are also included herein. When a specific embodiment is described herein with regard to the present invention, the specification discloses not only the embodiment itself, but also inventions that exclude the embodiment from the disclosed more generic inventions that comprise the embodiment.

Effects of the Invention

The present invention provides a molecular genetic technique for precisely modifying a gene sequence. The present invention is applicable in various occasions such as gene therapy, breed improvement, and biotechnological creation.

BRIEF DESCRIPTION OF DRAWINGS

FIG. 1A shows a donor polynucleotide carrying a single DNA cleavage site on the 5' side of a normal gene locus with respect to the disease-causing mutation site and carrying a selection marker gene and an exclusion marker gene in the linker polynucleotide. FIG. 1B shows conversion of the pre-modification nucleotide sequence to the post-modification nucleotide sequence. FIG. 1C shows the resulting modified gene.

FIG. 2A shows a donor plasmid carrying a molecular marker in which the sequence at and around the SexA1 site (ACCAGGT) on exon 2 is to be synonymously converted. FIG. 2B shows conversion of the pre-modification nucleotide sequence to the post-modification nucleotide sequence. FIG. 2C shows the result of gene modification. FIG. 2D shows initiation of operational procedures by introduction of a linear donor plasmid treated with site-specific cleavage enzyme I-SceI to a cell carrying the target gene locus (SexA1 site). FIG. 2E shows obtaining cells carrying the vector-inserted target construct from hygromycin-resistant colonies by PCR screening. FIG. 2F shows yielding ganciclovir-resistant colonies after culturing and seeding the hygromycin-resistant clone.

FIG. 3A shows the structure of the region subjected to vector target insertion.

FIG. 3B shows detection with PCR of the upstream region (5' region) of the vector inserted target construct (left panel) and the downstream region (3' region) of the vector inserted target construct (right panel).

FIG. 4A shows release of a vector plasmid carrying the either the downstream sequence or the upstream sequence following replacement reaction from the vector-inserted target construct of FIG. 3A. FIG. 4B shows PCR analysis to confirm that the gene locus of the ganciclovir-resistant clone has a replaced structure (left panel), to confirm that a released plasmid does not exist in the cells of the ganciclovir-resistant clone (center panel), and to isolate a gene variant from the ganciclovir-resistant clones (right panel).

FIG. 5A depicts the problems to be solved by the invention. FIG. 5B depicts the means for solving the problems outlined in FIG. 5A. FIG. 5C shows that, by using the method of the present invention, problems such as On/Off-target inaccurate rejoining, residual site-specific recombination site (loxP and such), and loss of target cleavage sequence can be avoided.

DESCRIPTION OF EMBODIMENTS

Figure 1:
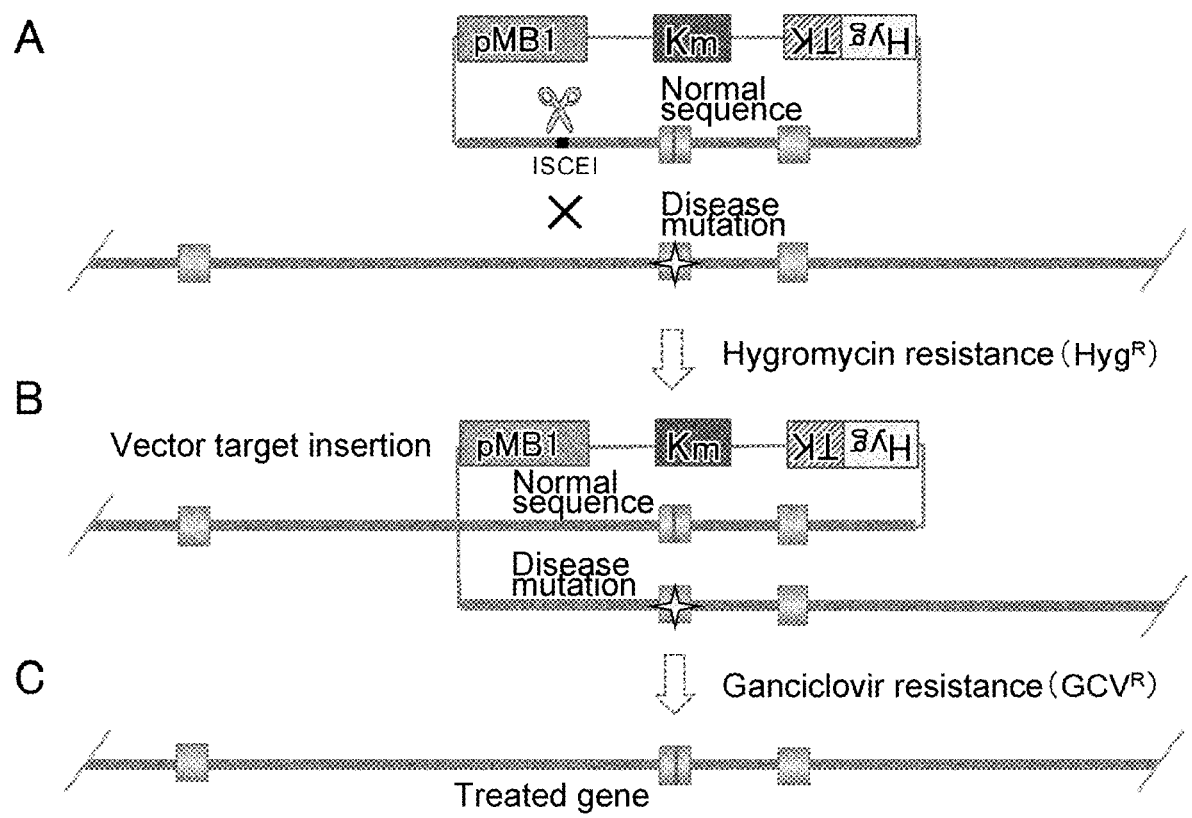
FIGS. 1A-C show the framework of the novel genome editing technique.

The present invention provides novel donor polynucleotides for modifying genomic sequences. The polynucleotide comprises a genomic fragment comprising one or more modification positions, wherein the two ends of the genomic fragment are linked by a polynucleotide (in this invention, this is called a linker polynucleotide), and the linker polynucleotide includes within it both a positive selection marker gene and a negative selection marker gene.

The species from which the genomic fragments are derived are not particularly limited, and for example, a desired eukaryotic genome is acceptable, and the genomic fragments may be derived from yeast, animal cells, plant cells, or such. Preferably, the genomic fragments are derived from animal cells, more preferably mammalian cells such as cells of primates, and specific examples include genomic fragments of mouse, rat, monkey, and human cells.

Furthermore, the genomic fragments can be cleaved at any position. This cleavable site may be cleaved such that it becomes both ends of the donor polynucleotide chain to produce a linear donor polynucleotide, or this site may stay linked in the donor polynucleotide so that the donor polynucleotide is circular. When the cleavable site is cleaved and the donor polynucleotide is linear, in that polynucleotide, the originally single genomic fragment becomes separated into two, and each of the two are bound to respective ends of the linker polynucleotide. That is, a structure in which the linker polynucleotide is sandwiched by a pair of genomic sequences is formed. When the donor polynucleotide is circular, one end of the genomic fragment is linked to one end of a linker polynucleotide, and the other end of the genomic fragment is linked to the other end of the linker polynucleotide, to form a circular structure.

The genomic fragment included in the donor polynucleotide may contain one or more modification positions. Herein, modification positions refer to positions having sequences different from those of positions corresponding to the genome carried by the target cells. These modification positions are different from the genomic sequences of cells which are to be subjected to genome editing, and by introducing this donor polynucleotide the genomic sequence of the target cells will be modified. The number of modification positions are not particularly limited, and there may be one or more, for example, two, three, four, five, ten, or more positions. Furthermore, each modification may be one or more nucleotide substitutions, nucleotide insertions, and/or nucleotide deletions, or combinations thereof.

As described above, both ends of the genomic fragment included in the donor polynucleotide are linked by a polynucleotide. The linker polynucleotide is linked so that a continuous double-stranded nucleic acid is formed with the genomic fragment. The sequence of the linker polynucleotide is not particularly limited, and for example, it may be a sequence derived from a plasmid vector, phage vector, cosmid vector, viral vector, artificial chromosome vector (for example, a yeast artificial chromosome (YAC) vector, and a bacterial artificial chromosome (BAC) vector), or such. This way, when the linker polynucleotide has a vector backbone and functions as a vector, the donor polynucleotide of the present invention may be called a donor vector. When the vector is a plasmid vector, the donor polynucleotide of the present invention may also be called a donor plasmid. The donor polynucleotide which functions as a vector may be retained in an appropriate host (cells or *Escherichia coli*). Furthermore, when the vector is replication-competent, the donor polynucleotide may be replicated in a host. The donor polynucleotide of the present invention preferably has autonomous replication ability in an appropriate host.

The linker polynucleotide may contain in it the genomic sequence of a cell to be subjected to genome editing; however, as described above, the target genomic sequence which is to be modified is only the genomic sequence linked to both ends of the linker polynucleotide, and the genomic sequences which may be included in the linker polynucleotide are not the target sequences which are to be modified.

The length of the linker polynucleotide is not particularly limited, and it may be a polynucleotide having an appropriate and suitable length. When using a vector backbone as the linker polynucleotide, the length of the linker polynucleotide may change depending on the type of vector used. In one example, the length of the linker polynucleotide (length including the later-described positive selection marker gene and the negative selection marker gene) may be, for example, 1 kb or more, 2 kb or more, 3 kb or more, 5 kb or more, 7 kb or more, 10 kb or more, 20 kb or more, or 30 kb or more. Furthermore, the length may be 100 kb or less, 800 kb or less, 70 kb or less, 60 kb or less, 50 kb or less, 40 kb or less, 30 kb or less, 20 kb or less, 10 kb or less, or 8 kb or less.

In the present invention, the linker polynucleotide contains a positive selection marker gene and a negative selection marker gene. Here, a positive selection marker gene refers to a gene encoding a marker used to select cells carrying this marker (and/or to remove cells that do not have this marker), and a negative selection marker gene refers to a gene encoding a marker used to remove cells carrying this marker (and/or to select cells that do not have this marker). The positive selection marker gene and the negative selection marker gene can be selected appropriately. Examples of the positive selection marker gene include various drug-resistance genes such as Hyg (hygromycin-resistance gene), Puro (puromycin resistance gene), and β-geo (a fusion gene for β galactosidase and neomycin resistance genes), but are not limited thereto. Examples of a negative selection marker gene include genes that directly or indirectly induce inhibition of survival or growth of cells, and specific examples are herpes simplex virus-derived thymidine kinase (TK) gene, diphtheria toxin A fragment (DT-A) gene, and cytosine deaminase (CD) gene, but are not limited thereto.

Donor polynucleotides used in conventional genome editing generally carry a positive selection marker gene in a genomic fragment included in the donor polynucleotide, and when placing a negative selection marker gene, it is placed outside of the genomic fragment. In contrast, donor polynucleotides of the present invention have the feature of containing both a positive selection marker gene and a negative selection marker gene in the linker polynucleotide. More specifically, a genomic sequence of the target cell may or may not be included between the positive selection marker gene and the negative selection marker gene, and if it is included, it is preferably short enough so that recombination does not take place. The length of such a genomic sequence is for example, not more than 1.0 kb, not more than 0.8 kb, not more than 0.6 kb, not more than 0.5 kb, not more than 0.4 kb, not more than 0.3 kb, not more than 0.2 kb, or not more than 0.1 kb.

The positive selection marker gene and the negative selection marker gene included in the linker polynucleotide are preferably positioned close to each other. If the two are closely positioned, recombination between the positive selection marker gene and the negative selection marker gene can be prevented from taking place (or suppressed to a sufficiently low frequency). For example, when the promoter sequence to the transcription termination sequence is regarded as a single gene, the region between the positive selection marker gene and the negative selection marker gene is, for example, not more than 10 kb, preferably not more than 8 kb, more preferably not more than 7 kb, not more than 5 kb, not more than 4 kb, not more than 3 kb, not more than 2 kb, not more than 1 kb, or not more than 0.5 kb.

More preferably, the positive selection marker and the negative selection marker are transcribed from the same promoter. Most preferably, the positive selection marker gene and the negative selection marker gene are fused, and the positive selection marker and the negative selection marker are expressed as a fusion protein.

As described above, a genomic fragment included in a donor polynucleotide is cleavable at any position. Herein, cleavable means that artificial cleavage can take place at that position. It is preferable that cleavage takes place uniquely at that position in the donor polynucleotide, and specifically, cleavage takes place only at that position in the donor polynucleotide.

Examples of the cleavable genomic fragment include cases where a restriction enzyme site is present in the genomic fragment. In that case, that position can be cleaved by the restriction enzyme. The restriction enzyme site is preferably included only at that site in the donor polynucleotide. Furthermore, by adding a cleavage sequence in the genomic fragment, that site can be made into a cleavable site. The cleavage sequence is not particularly limited, and a desired restriction enzyme cleavage sequence (for example, the NotI site), the meganuclease cleavage sequence (I-SceI site, PI-SceI site, or such), other cleavage enzyme recognition sequence, or such may be used. The cleavage enzyme may be a naturally occurring nuclease or an artificial nuclease. The cleavage may be a single-strand cleavage or a double-strand cleavage, but is preferably a double-strand cleavage. In the case of a double-strand cleavage, the cleavage site may form smooth ends, or 5' or 3' protruding ends. A nuclear localization signal (nls) may be added, when appropriate, to the nuclease. The nls amino acid sequence added to the NH$_2$ end of the I-SceI nuclease, as indicated in Example 3, is MDKAELI-PEPPKKKRKVELGT (SEQ ID NO: 42), but the nls sequence is not limited thereto.

Without being limited to the following, specific examples of cleavage sequences are those of the *Saccharomyces cerevisiae*-derived homing endonuclease I-SceI (GenBank: EU004203.1) and PI-SceI (GenBank: Z74233.1). When adding a cleavage sequence into the genomic fragment in the donor polynucleotide, the sequence is preferably not included in the sequence of the corresponding genomic fragment of the cell that will be subjected to administration of the donor polynucleotide, which corresponds to the genomic fragment included in the donor polynucleotide (that is, a genomic fragment carried by the cell before modification is performed by the donor polynucleotide, which is a region corresponding to the genomic fragment included in the donor polynucleotide). More preferably, the cleavage sequence is not included in the entire genome of the target cell, or is preferably, rationally and/or statistically expected to be included only at sufficiently low frequency (for example, at ten or fewer positions, five or fewer positions, three or fewer positions, two or fewer positions, or one or fewer positions in the entire genome).

The cleavage sequence of I-SceI is well known, and the 18-bp 5'-TAGGGATAACAGGGTAAT-3' (SEQ ID NO: 1) sequence is used (Colleaux, L. et al. Recognition and cleavage site of the intron-encoded omega transposase. Proc. Natl. Acad. Sci. USA 85, 6022-6026 (1988)). Even when this sequence is used as a Query to perform a BLAST SEARCH, a sequence that matches this sequence is not found from the human genome sequences in the database and in the transcription products.

The positional relationship between one or more modification positions (modification positions of interest) and the cleavable site included in the genomic fragment of the donor polynucleotide is not particularly limited, but preferably, all of the modification positions are concentrated on one side of the cleavable site. This way, when homologous recombination takes place with the target cell genome near the cleavage site of the donor polynucleotide, multiple modification positions will be recombined together without becoming separated; therefore, cells introduced with multiple modification positions of interest can be obtained in one operation.

As described later, in a cell carrying the target-inserted structure formed by introduction of the donor polynucleotide into the cell's genome, the genome carrying the modification position and the genome originally carried by the cell will be positioned before and after the linker polynucleotide and will be serially arranged in no particular order; however, when further recombination occurs naturally and the linker polynucleotide is removed from this cell, parts of the genomic sequence positioned before and after it will be removed as well. The present invention includes both embodiments in which the cleavable site is positioned in the upstream side (more specifically, 5' side in terms of the sense strand of the gene which will be subjected to modification) or the downstream side (more specifically, 3' side in terms of the sense strand of the gene which will be subjected to modification) of the modification position in the genomic fragment included in the donor polynucleotide.

The length of a genomic fragment included in a donor polynucleotide is not particularly limited, and when introduced into cells, as long as the length is sufficient to cause homologous recombination with the genome of the cells, a fragment having a desired length may be used. The length of a genomic fragment included in a donor polynucleotide is, for example, 0.05 kb or more, 0.5 kb or more, 1 kb or more, 1.5 kb or more, 2 kb or more, 3 kb or more, 4 kb or more, or 5 kb or more, and for example, 10000 kb or less, 5000 kb or less, 500 kb or less, 300 kb or less, 200 kb or less, 100 kb or less, 80 kb or less, 50 kb or less, 30 kb or less, 20 kb or less, or 10 kb or less. By enlarging a genome fragment included in a donor polynucleotide to several tens of kb or several hundreds of kb or so, corresponding to the size of one gene locus, a plurality of mutation positions over a wide range can be modified together. A donor polynucleotide of the present invention may include such a long genomic fragment.

The sequence of a genomic fragment included in a donor polynucleotide has high sequence identity with the corresponding genomic sequence of the target cell, and this induces homologous recombination with the genome of the target cell. For example, the sequence of a genomic fragment excluding the modification position and the cleavage site may have sequence identity to the sequence of a corresponding fragment of the genome of the target cell, which is ordinarily 90% or more, preferably 95% or more, 96% or more, 97% or more, 98% or more, 99% or more, or 100%.

The length from a cleavable site of a genomic fragment included in a donor polynucleotide to its closest modification position is ordinarily 10 bases or more, preferably 20 bases or more, 30 bases or more, 40 bases or more, 50 bases or more, 80 bases or more, 100 bases or more, 200 bases or more, 300 bases or more, 400 bases or more, 500 bases or more, 800 bases or more, or 1 kb or more. Furthermore, it is ordinarily not more than 10000 kb, not more than 5000 kb, not more than 500 kb, not more than 100 kb, or preferably, not more than 80 kb, not more than 70 kb, not more than 60 kb, not more than 50 kb, not more than 40 kb, not more than 30 kb, not more than 20 kb, not more than 10 kb, not more than 8 kb, not more than 7 kb, not more than 6 kb, or not more than 5 kb. Furthermore, in a genomic fragment included in a donor polynucleotide, the length from the modification position closest to the linker polynucleotide to the site of linkage with the linker polynucleotide is similar to the above.

More specifically, the length from a cleavable site of a genomic fragment included in a donor polynucleotide, to its closest modification position is preferably, for example, 100 bases or more, 150 bases or more, 200 bases or more, 250 bases or more, 300 bases or more, 316 bases or more, 350 bases or more, 400 bases or more, 500 bases or more, 600 bases or more, 1000 bases or more, 1200 bases or more, 1500 bases or more, or 1960 bases or more. Furthermore, in a genome fragment included in a donor polynucleotide, the length from the cleavable site closest to the linker polynucleotide to the site of linkage with that linker polynucleotide is preferably, for example, 200 bases or more, 250 bases or more, 300 bases or more, 316 bases or more, 350 bases or more, 400 bases or more, 500 bases or more, 600 bases or more, 1000 bases or more, 1200 bases or more, 1500 bases or more, 1960 bases or more, 2000 bases or more, 2244 bases or more, or 2560 bases or more.

Furthermore, the present invention relates to methods for modifying the genomic sequence of cells using a donor polynucleotide of the present invention. The method comprises the steps of: (a) introducing a donor polynucleotide of the present invention into cells; (b) selecting the cells introduced with the donor polynucleotide by using a positive selection marker; and (c) selecting cells from which the linker polynucleotide has been removed by using a negative selection marker. The method is carried out, for example, outside of a living body (for example, in vitro or ex vivo).

In the present invention, carrying out the method in vitro includes carrying out the method ex vivo.

The cells to which a donor polynucleotide is introduced are cells having in their genome a sequence with high sequence identity to the sequence of the genomic fragment included in the donor polynucleotide, and ordinarily, they are cells of the same species as the organism from which the genomic fragment included in the donor polynucleotide is derived. Such cells may be, for example, cells of a desired eukaryote, and examples include animal cells or plant cells, preferably animal cells, and more preferably mammalian cells such as cells of primates, and specific examples include mouse, rat, monkey, and human cells. Furthermore, the types of cells are not particularly limited, and cells of desired tissues can be used, and genome modification can be performed by introducing a donor polynucleotide to differentiated or undifferentiated cells, precursor cells, progenitor cells, or such. Furthermore, introduction to pluripotent stem cells (for example, induced pluripotent stem cells (iPS cells)) is also possible.

The donor polynucleotide introduced into cells may be circular or linear. When introducing a linear donor polynucleotide, the cleavable site of the genomic fragment in the donor polynucleotide is cleaved to make a straight chain, and then this is introduced into cells. The method for cleaving the site is not particularly limited, and for example, a nuclease cleavage site can be cleaved using that nuclease. After cleavage, preferably the donor polynucleotide is purified for nuclease removal and such, or the nuclease is inactivated before its introduction into cells.

When introducing a circular donor polynucleotide, the cleavable site of the genomic fragment in the donor polynucleotide is cleaved when introducing the polynucleotide into cells or after the introduction. To cleave the site, a nuclease that cleaves this site can be introduced into or expressed in cells. For nuclease expression, for example, a vector encoding the nuclease may be introduced into the cells.

When expressing a nuclease in cells, the timing is not particularly limited as long as the donor polynucleotide contacts with the nuclease in the cells and the cleavage reaction takes place, and the expression may be before, during, or after introduction of the donor polynucleotide into the cells. Preferably the nuclease is expressed within 48 hours before to 48 hours after introduction of the donor polynucleotide into cells, and more preferably, it is expressed within 24 hours before to 24 hours after the introduction. Furthermore, the nuclease is preferably allowed to express within 48 hours before to 48 hours after introduction of the donor polynucleotide into cells, and is more preferably allowed to express within 24 hours before to 24 hours after the introduction. For example, by introducing a vector for expressing the nuclease and the donor polynucleotide simultaneously into cells, genome editing can be accomplished efficiently. When expressing the nuclease using a vector, considering the time lag until the expression level is sufficiently elevated, the vector may be introduced into cells before introducing the donor polynucleotide into the cells.

Introduction of a vector for expressing a donor polynucleotide and/or a nuclease into cells can be appropriately carried out by a well-known method, and is not particularly limited. The introduction can be carried out using, for example, lipofection, electroporation, microinjection, particle gun method, and viral vector method.

When using viral vectors for expression of nucleases, desired viral vectors, such as retroviral vectors, adenoviral vectors, adeno-associated viral vectors, and vaccinia virus vectors, may be used. Viral vectors particularly suitably used in the present invention include minus-strand RNA virus vectors, and for example, paramyxovirus vectors can be suitably used. Paramyxovirus refers to viruses that belong to the family Paramyxoviridae, and to viruses derived from them. Paramyxoviridae includes the subfamily Paramyxovirinae (comprising the genus Respirovirus (also called the genus Paramyxovirus), the genus Rubulavirus and the genus Morbillivirus), and the subfamily Pneumovirinae (comprising the genus Pneumovirus and the genus Metapneumovirus). Specifically, viruses included in the Paramyxoviridae family viruses are the Sendai virus, Newcastle disease virus, Mumps virus, Measles virus, Respiratory syncytial virus, rinderpest virus, distemper virus, simian parainfluenza virus (SV5), human parainfluenza virus type 1, 2, and 3, and such. More specifically, for example, the Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MeV), rinderpest virus (RPV), Hendra virus (Hendra), Nipah virus (Nipah), human parainfluenza virus-2 (HPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV) are included. Rhabdoviruses include the Vesicular stomatitis virus, Rabies virus, and such of the family Rhabdoviridae.

The minus-strand RNA viruses may be derived from natural strains, wild-type strains, mutant strains, laboratory-passaged strains, artificially constructed strains, or such. Examples of Sendai virus include the Z strain, but are not limited thereto (Medical Journal of Osaka University Vol. 6, No. 1, March 1955 p 1-15). For example, the viruses can have mutations or deletions in any of the genes carried by the wild-type viruses. For example, viruses lacking propagation ability, which comprise mutations such as a deletion in at least a viral envelope protein or coat protein-encoding gene or stop codon mutations that inhibit expression of those genes, can be preferably used. For example, such viruses that do not express envelope proteins can replicate the genome in infected cells but cannot form infectious virions. Such viruses lacking propagation ability are particularly suitable as highly safe vectors. For example, a virus that does not have the gene encoding envelope protein (spike protein) F or HN, or a virus that does not encode the F and HN genes in its genome can be used (WO00/70055 and WO00/70070; Li, H.-O. et al., J. Virol. 74(14) 6564-6569 (2000)). Viruses can replicate a genome in the infected cells if at least the proteins that are necessary for genome replication (for example N, P, and L proteins) are encoded in the genomic RNA. To produce virions which lack envelope proteins and are infectious, products of the deficient genes or proteins which can complement the deficient genes are supplied from the outside to virus-producing cells (WO00/70055 and WO00/70070; Li, H.-O. et al., J. Virol. 74(14) 6564-6569 (2000)). On the other hand, non-infectious virions can be collected by not complementing the missing viral proteins at all (WO00/70070).

Furthermore, as a viral vector, the use of viral vectors carrying a mutant viral protein gene is also preferred. For example, in the envelope proteins and coat proteins, many mutations including attenuation mutations and temperature-sensitive mutations are known. Viruses having these mutant protein genes can be used suitably in the present invention. In the present invention, vectors with lowered cytotoxicity are desirably used. For example, many mutations including attenuation mutations and temperature-sensitive mutations are known in viral structural proteins (NP, M) and RNA synthases (P, L). Paramyxovirus vectors having these mutant protein genes, and such can be suitably used in the present invention depending on the purpose.

Specifically, examples of preferred mutations of the M gene of Sendai viruses include amino acid substitutions at a site arbitrarily selected from the group consisting of position 69 (G69), position 116 (T116), and position 183 (A183) in the M protein (Inoue, M. et al., J. Virol. 2003, 77: 3238-3246). Viruses having a genome encoding a mutant M protein, in which the amino acids of any one site, preferably a combination of any two sites, or more preferably all three sites of the three sites mentioned above in the Sendai virus M protein are substituted to other amino acids, are used suitably in the present invention.

Preferred amino acid mutations are substitution to other amino acids with a side chain having different chemical properties, and examples are substitution to an amino acid with a BLOSUM62 matrix (Henikoff, S. and Henikoff, J. G. (1992) Proc. Natl. Acad. Sci. USA 89: 10915-10919) score of three or less, preferably two or less, more preferably one or less, and even more preferably 0. Specifically, G69, T116, and A183 of the Sendai virus M protein can be substituted to Glu (E), Ala (A), and Ser(S), respectively. Alternatively, mutations homologous to mutations in the M protein of the temperature-sensitive P253-505 measles virus strain (Morikawa, Y. et al., Kitasato Arch. Exp. Med. 1991: 64; 15-30) can also be used. Mutations can be introduced according to known mutation introducing methods, for example, using oligonucleotides and such.

Furthermore, examples of preferred mutations in the HN gene include amino acid substitution of a site arbitrarily selected from the group consisting of position 262 (A262), position 264 (G264), and position 461 (K461) of the HN protein of a Sendai virus (Inoue, M. et al., J. Virol. 2003, 77: 3238-3246). Viruses having a genome encoding a mutant HN protein in which the amino acids of any one of the three sites, preferably a combination of any two sites, or more preferably all three sites are substituted to other amino acids are used suitably in the present invention. As mentioned above, preferred amino acid substitutions are substitution to other amino acids with a side chain having different chemical properties. As a preferred example, A262, G264, and K461 of the Sendai virus HN protein can be substituted to Thr (T), Arg (R), and Gly (G), respectively. Furthermore, for example, using the temperature-sensitive vaccine strain Urabe AM9 of the mumps virus as a reference, amino acids of positions 464 and 468 of the HN protein can be mutated (Wright, K. E. et al., Virus Res. 2000: 67; 49-57).

Furthermore, Sendai viruses may have mutations in the P gene and/or the L gene. Examples of such mutations are specifically, mutation of Glu at position 86 (E86) in the SeV P protein, and substitution of Leu at position 511 (L511) in the SeV P protein to other amino acids. As mentioned above, preferred amino acid substitutions are substitutions to other amino acids with a side chain having different chemical properties. Specific examples include substitution of the amino acid at position 86 to Lys, and substitution of the amino acid at position 511 to Phe. Furthermore, examples in the L protein include substitution of Asn at position 1197 (N1197) and/or Lys at position 1795 (K1795) in the SeV L protein to other amino acids, and similarly as above, preferred amino acid substitutions are substitutions to other amino acids with a side chain having different chemical properties. Specific examples are substitution of the amino acid at position 1197 to Ser, and substitution of the amino acid at position 1795 to Glu. Mutations of the P gene and L gene can significantly increase the effects of sustained infectivity, suppression of release of secondary particles, or suppression of cytotoxicity. Further, combination of mutations and/or deletions of envelope protein genes can dramatically increase these effects. Furthermore, examples for the L gene include substitution of Tyr at position 1214 (Y1214) and/or substitution of Met at position 1602 (M1602) of the SeV L protein to other amino acids, and similarly as above, preferred amino acid substitutions are substitutions to other amino acids with a side chain having different chemical properties. Specific examples are substitution of the amino acid at position 1214 to Phe, and substitution of the amino acid at position 1602 to Leu. The above-mentioned exemplary mutations can be arbitrarily combined.

For example, Sendai virus vectors in which at least G of position 69, T of position 116, and A of position 183 of the SeV M protein, at least A of position 262, G of position 264, and K of position 461 of the SeV HN protein, at least L of position 511 of the SeV P protein, and at least N of position 1197 and K of position 1795 of the SeV L protein are each substituted to other amino acids, and in which the F gene is also deficient or deleted; and F-gene-deleted or -deficient Sendai virus vectors whose cytotoxicity is similar to or lower than of those mentioned above and/or inhibition of NTVLP formation at 37° C. is similar to or higher than of those mentioned above are suitable in the present invention.

More specifically, Sendai virus vectors in which the F gene is deleted, and the genome contains G69E, T116A, and A183S mutations of the M protein, A262T, G264R, and K461G mutations of the HN protein, L511F mutation of the P protein, and N1197S and K1795E mutations of the L protein, can be used suitably in the present invention. In the present invention the combination of F gene deletion and these mutations is denoted as "TSΔF".

For example, in the case of Sendai viruses (SeV), examples of mutations of the L protein include substitutions of amino acids at sites arbitrarily selected from position 942 (Y942), position 1361 (L1361), and position 1558 (L1558) of the SeV L protein to other amino acids. Similarly as above, preferred amino acid substitutions are substitution to other amino acids with a side chain having different chemical properties. Specific examples include substitution of the amino acid at position 942 to His, substitution of the amino acid at position 1361 to Cys, and substitution of the amino acid at position 1558 to Ile. In particular, the L protein with substitution at least at position 942 or 1558 can be used preferably. For example, mutant L proteins in which, in addition to position 1558, position 1361 is also substituted to another amino acid are preferred as well. Furthermore, mutant L proteins in which, in addition to position 942, position 1558 and/or position 1361 are also substituted to other amino acids are suitable as well. These mutations can increase the temperature sensitivity of the L protein.

Examples of mutations of the P protein include substitutions of amino acids at sites arbitrarily selected from position 433 (D433), position 434 (R434), and position 437 (K437) of the SeV P protein to other amino acids. Similarly as above, preferred amino acid substitutions are substitution to other amino acids with a side chain having different chemical properties. Specific examples include substitution of the amino acid at position 433 to Ala (A), substitution of the amino acid at position 434 to Ala (A), and substitution of the amino acid at position 437 to Ala (A). In particular, P proteins in which all three of these sites are substituted can be used suitably. These mutations can increase the temperature sensitivity of the P protein.

F-gene-deleted or -deficient Sendai virus vectors encoding a mutant P protein in which at least at the three positions D at position 433, R at position 434, and K at position 437 of the SeV P protein are substituted to other amino acids, and a mutant L protein in which at least the L at position 1558 of the SeV L protein is substituted (preferably a mutant L protein in which at least the L at position 1361 is also substituted to another amino acid); and F-gene-deleted or -deficient Sendai virus vectors whose cytotoxicity is similar to or lower than of those mentioned above and/or whose temperature sensitivity is similar to or higher than of those mentioned above are used suitably in the present invention. In addition to the mutations presented as examples herein, each of the viral proteins may have mutations on other amino acids (for example, on ten or less, five or less, four or less, three or less, two or less, or one amino acid). Since vectors comprising the above-mentioned mutations show a high temperature sensitivity, the vectors can be removed easily by culturing the cells at an ordinary temperature (for example, approximately 37° C., specifically 36.5° C. to 37.5° C., preferably 36.6° C. to 37.4° C., and more preferably 36.7° C. to 37.3° C.). For vector removal, culturing at a slightly high temperature (for example, 37.5° C. to 39° C., preferably 38° C. to 39° C., or 38.5° C. to 39° C.) is also acceptable.

Specific examples of the vectors include Sendai virus vectors in which the F gene is deleted, and the genome contains G69E, T116A, and A183S mutations of the M protein, A262T, G264R, and K461G mutations of the HN protein, L511F mutation of the P protein, and N1197S and K1795E mutations of the L protein.

Preferably, examples of the vectors include Sendai virus vectors in which the F gene is deleted, and the genome contains G69E, T116A, and A183S mutations of the M protein, A262T, G264R, and K461G mutations of the HN protein, L511F mutation of the P protein, and N1197S and K1795E mutations of the L protein, and additionally the following mutations of (i) and/or (ii):
 (i) D433A, R434A, and K437A mutations of the P protein;
 (ii) Y942H, L1361C, and/or L1558I mutations of the L protein.

More specific examples of the vectors include Sendai virus vectors in which the F gene is deleted, and the genome contains G69E, T116A, and A183S mutations of the M protein, A262T, G264R, and K461G mutations of the HN protein, L511F mutation of the P protein, and N1197S and K1795E mutations of the L protein, and additionally any one of the following mutations:
 (i) D433A, R434A, and K437A mutations of the P protein; and L1361C and L1558I mutations of the L protein (TS15):
 (ii) D433A, R434A, and K437A mutations of the P protein (TS12);
 (iii) Y942H, L1361C, and L1558I mutations of the L protein (TS7);
 (iv) D433A, R434A, and K437A mutations of the P protein; and L1558I mutation of the L protein (TS13); and
 (v) D433A, R434A, and K437A mutations of the P protein; and L1361C mutation of the L protein (TS14).

When a vector is loaded with a nuclease gene, the nuclease gene can be inserted immediately before (3' side of the genome) or immediately after (5' side of the genome) any one of the virus genes (NP, P, M, F, HN, or L). For example, but without being limited thereto, the gene may be integrated immediately after the Sendai virus P gene, or more specifically, immediately downstream of the P gene (immediately to the 5' side of the minus-strand RNA genome).

For example, production of the minus-strand RNA viruses can be carried out by using the following known methods (WO97/16539; WO97/16538; WO00/70055; WO00/70070; WO01/18223; WO03/025570; WO2005/071092; WO2006/137517; WO2007/083644; WO2008/007581; Hasan, M. K. et al., J. Gen. Virol. 78: 2813-2820, 1997; Kato, A. et al., 1997, EMBO J. 16: 578-587 and Yu, D. et al., 1997, Genes Cells 2: 457-466; Durbin, A. P. et al., 1997, Virology 235: 323-332: Whelan, S. P. et al., 1995, Proc. Natl. Acad. Sci. USA 92: 8388-8392; Schnell. M. J. et al., 1994, EMBO J. 13: 4195-4203; Radecke, F. et al., 1995, EMBO J. 14: 5773-5784; Lawson, N. D. et al., Proc. Natl. Acad. Sci. USA 92: 4477-4481: Garcin, D. et al., 1995, EMBO J. 14: 6087-6094: Kato, A. et al., 1996, Genes Cells 1: 569-579: Baron, M. D. and Barrett, T., 1997, J. Virol. 71: 1265-1271: Bridgen, A. and Elliott, R. M., 1996, Proc. Natl. Acad. Sci. USA 93: 15400-15404; Tokusumi, T. et al. Virus Res. 2002: 86; 33-38; and Li, H.-O. et al., J. Virol. 2000: 74; 6564-6569). Regarding methods for proliferation of viruses and methods for producing recombinant viruses, see "Uirusu-gaku Jikken-gaku Kakuron (Detailed Virology Experiments)", second revised edition (National Institute of Health Students Union edition, Maruzen, 1982).

In the methods of the present invention, the step of introducing a donor polynucleotide into cells (step (a)) is followed by selecting cells carrying the linker polynucleotide (that is, the cells carrying the donor polynucleotide) using a positive selection marker (step (b)). This step can be performed appropriately according to the type of marker. For example, when using a drug resistance marker, cells are cultured with the drug, and cells expressing the marker are selected. Selection of the cells may be completely separating the cell population expressing the positive selection marker from the cell population not expressing the marker, or it may be increasing the proportion of the positive selection marker-expressing cells. This selection significantly increases the proportion of positive selection marker-positive cells (or the donor polynucleotide-introduced cells) among all of the cells. For example, the selection increases the proportion of positive selection marker-positive cells (or the donor polynucleotide-introduced cells) among all of the cells by 10-fold or more, 50-fold or more, 100-fold or more, 500-fold or more, 1000-fold or more, 5000-fold or more, 10000-fold or more, 50000-fold or more, or 100000-fold or more. Furthermore, the selection preferably causes the proportion of positive selection marker-positive cells (or the donor polynucleotide-introduced cells) among all of the cells to be 0.0000001 or more, 0.000001 or more, 0.00001 or more, 0.0001 or more, 0.001 or more, 0.01 or more, 0.02 or more, 0.05 or more, 0.1 or more, 0.2 or more, 0.3 or more, 0.4 or more, 0.5 or more, 0.6 or more, 0.7 or more, 0.8 or more, 0.9 or more, 0.95 or more, 0.98 or more, or 0.99 or more.

When a donor polynucleotide of the present invention is integrated into the genome of a cell by homologous recombination, the region will have the following structure: (a) genomic fragment originally carried by the cell-(b) genomic fragment included in the donor polynucleotide-(c) linker polynucleotide included in the donor polynucleotide-(d) genomic fragment included in the donor polynucleotide-(e) genomic fragment originally carried by the cell. However, when the genomic fragment included in the donor polynucleotide is the same as the genome of the cell except for the modification position of interest, seemingly, through the linker polynucleotide included in the donor polynucleotide, the structure formed will have nearly the same genomic sequences lined up before and after the linker polynucleotide. In the present invention, such a structure is called a target-inserted structure of the donor polynucleotide. Which of the genomic fragments lined up before and after the linker polynucleotide includes the modification of interest (that is, the modified sequence included in the donor polynucleotide) may change depending on the position where homologous recombination took place; however, in any case, a structure in which the genomic fragment containing the modification of interest and the genomic fragment originally carried by the cell are serially lined up through a linker polynucleotide is formed. Furthermore, the linker polynucleotide includes a positive selection marker gene and a negative selection marker gene. More specifically, a cell obtained by the method of the present invention is a cell having a structure that has a donor polynucleotide of the present invention integrated into its genome, wherein a modified genomic fragment included in the donor polynucleotide and a fragment corresponding to it, which is derived from the genome of the cell, take a structure in which they are serially arranged in no particular order through the linker polynucleotide included in the donor polynucleotide, and the linker polynucleotide comprises within it a positive selection marker gene and a negative selection marker gene.

In the method of the present invention, the next step is selecting the cells from which the linker polynucleotide has been removed by using the negative selection marker. As described above, when a donor polynucleotide of the present invention is introduced to the genome of a cell by homologous recombination, the genomic fragment containing the modification of interest and the genomic fragment originally carried by the cell form a structure in which they are tandemly lined up through a linker polynucleotide. This pair of sequences is highly homologous, and therefore homologous recombination is induced highly efficiently, and as a result, the fragment containing the linker polynucleotide is removed from the genome. There is no need to carry out any special operation to induce this reaction. Culturing the cells generates cells from which the linker polynucleotide has been removed. Furthermore, by using the negative selection marker gene in the linker polynucleotide, cells from which the linker polynucleotide has been removed from the genome can be selected actively.

This step can be performed appropriately according to the type of the negative selection marker. For example, when using a thymidine kinase (TK) gene, cells are cultured with ganciclovir, and cells not expressing the marker (or cells from which the linker polynucleotide has been removed) are selected. Selection of the cells may be completely separating the cell population not expressing the negative selection marker (or cells from which the linker polynucleotide has been removed) from the cell population expressing the negative selection marker (or cells from which the linker polynucleotide has not been removed), or it may be increasing the proportion of cells not expressing the negative selection marker (or cells from which the linker polynucleotide has been removed). This selection significantly increases the proportion of cells not expressing the negative selection marker (or cells from which the linker polynucleotide has been removed) among all of the cells. For example, the selection increases the proportion of cells not expressing the negative selection marker (or cells from which the linker polynucleotide has been removed) among all of the cells by 10-fold or more, 50-fold or more, 100-fold or more, 500-fold or more, 1000-fold or more, 5000-fold or more, 10000-fold or more, 50000-fold or more, or 100000-fold or more. Furthermore, the selection preferably causes the proportion of cells not expressing the negative selection marker (or cells from which the linker polynucleotide has been removed) among all of the cells to be 0.00001 or more, 0.0001 or more, 0.001 or more, 0.01 or more, 0.02 or more, 0.05 or more, 0.1 or more, 0.2 or more, 0.3 or more, 0.4 or more, 0.5 or more, 0.6 or more, 0.7 or more, 0.8 or more, 0.9 or more, 0.95 or more, 0.98 or more, or 0.99 or more.

In the cells obtained by selection using the negative selection marker, the genomic fragments that were tandemly lined up before and after the linker polynucleotide as a result of homologous recombination are restored as a single copy. The thus obtained cells are expected to have its linker polynucleotide portion completely removed; however, which part of the overlapping genomic sequence region is removed may change depending on the position where recombination takes place. Therefore, a mixture of cells introduced with the intended genomic modification and cells without introduction of modifications (more specifically, cells that returned to its original state) is present in the obtained cells. However, stochastically these cells will appear in nearly equal amounts, and thus, cells that retain the intended modifications can be easily obtained. Whether or not the cells have the modification of interest can be identified, for example, by directly or indirectly detecting a sequence specific to the modification position of interest, and for example, by confirming the nucleotide sequence by amplifying the target site by PCR, or by confirming the presence or absence of PCR products, length of the amplification fragment, and such by performing PCR using primers specific to the mutated site, and such.

Genetic modification of the present invention will be described in further detail below.

FIG. 1 shows the genetic modification scheme according to one embodiment of the present invention. Here, the donor polynucleotide is also referred to as the vector, donor plasmid, or such. In the first step (FIG. 1A-B), a vector-inserted target structure is constructed in the target gene, in which the backbone region of the donor plasmid is sandwiched between the post-modification nucleotide sequence and the pre-modification nucleotide sequence so that the post-modification nucleotide sequence and the pre-modification nucleotide sequence are arranged in tandem (in no particular order). In the second step (FIG. 1 B-C), the pre-modification nucleotide sequence is converted to the post-modification nucleotide sequence by selecting clones in which the vector-inserted target structure has been spontaneously replaced with a single structure having only the modified nucleotide sequence, and this causes the gene to be modified.

In A, the vector backbone of the donor plasmid is indicated by a thin line, and the sequence homologous to the modification gene in which the post-modification sequence of the donor plasmid is positioned near the center is indicated by a thick line, and the gene locus to be modified in the cell is shown below the plasmid. This indicates that when the donor plasmid is introduced to the cell carrying the gene locus to be modified, the respective homologous regions of the gene locus to be modified and the donor plasmid become aligned. The genomic sequence carried by the cell contains a disease mutation, and the genomic fragment carried by the donor plasmid carries the normal sequence.

In B, after alignment of the homologous regions, homologous recombination reaction starts from the cleaved ends produced by I-SceI and such, and as a result, a vector-inserted target construct is formed. It is shown that in this structure, the fragment containing the post-modification sequence (normal sequence) and the fragment containing the pre-modification sequence (disease mutation) are arranged in tandem with the vector backbone (linker polynucleotide) sandwiched between them. The cell clone carrying the vector-inserted target construct is isolated, for example, as a hygromycin-resistant clone.

C shows the conversion of the pre-modification nucleotide sequence to the post-modification nucleotide sequence through spontaneous replacement from this vector-inserted target structure to the single structure having only the post-modification nucleotide sequence. This replaced cell clone is isolated, for example, as a ganciclovir-resistant clone. This way, cells carrying the vector-inserted target structure, which is the product of the above-described first step (that is, a structure in which the fragment containing the post-modification sequence (normal sequence) and the fragment containing the pre-modification sequence (disease mutation) are arranged in tandem with the vector backbone (linker polynucleotide) sandwiched between them), are cell strains carrying the vector-inserted target structure in which the pre-modification nucleotide sequence is spontaneously replaced to the post-modification nucleotide sequence to thereby allow conversion of the pre-modification nucleotide sequence to a single structure having only the post-modification nucleotide sequence.

The vector backbone of the donor polynucleotide used in the Examples of this application contains the *E. coli* DNA replication origin (pMB1), the kanamycin resistance gene (*E. coli* selection marker; Km), and the fusion gene (HygTK) comprising the hygromycin resistance gene (animal cell selection marker) and HSV-TK (animal cell exclusion marker) under the control of a human transcription start site. Sequence homologous to the modification gene is composed of a 5488-bp fragment covering intron 1 of the human HPRT gene, exon 2 carrying the post-modification sequence (normal sequence), intron 2, exon 3, and intron 3, and the gene locus to be modified has the pre-modification sequence (disease mutation; indicated by a cross-shaped star) in exon 2, which is the subject of modification.

Figure 2:
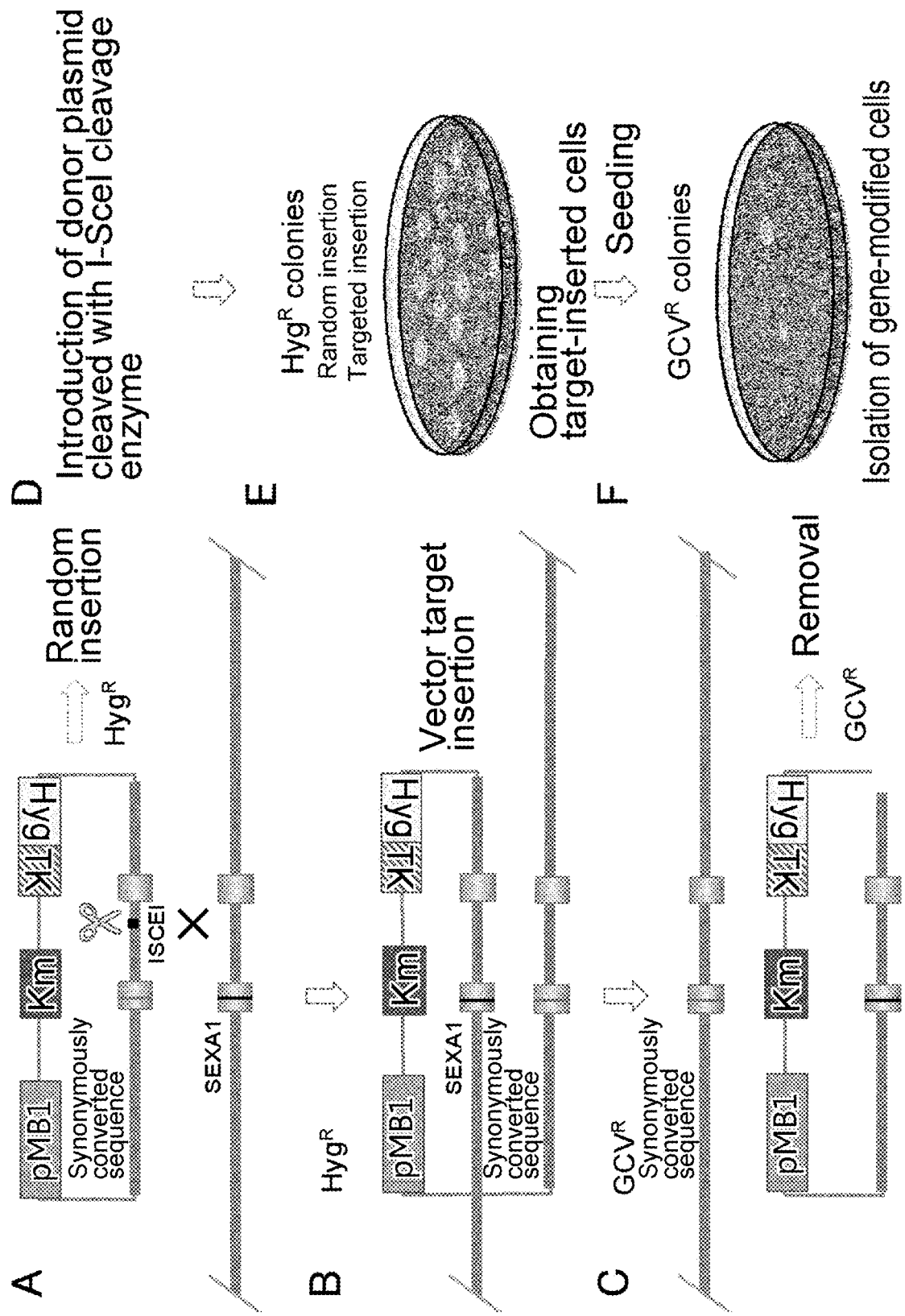
FIGS. 2A-F show the demonstration experiment for-gene modification by the novel genome editing technique.

FIG. 2 shows the procedure of the demonstration experiment for genetic modification by the genome editing technique of the present invention. A to C show a genetic modification scheme similar to FIG. 1. Since the donor plasmid carries a molecular marker in which the sequence at and around the SexA1 site (ACCAGGT) on exon 2 has been synonymously converted, sequence modification of the target gene locus region can be confirmed by the change from the SexA1 site to the synonymously converted sequence. D to F show the operational procedures that accompany the reactions from A to C. The linear donor plasmid (synonymously converted sequence) treated with the site-specific cleavage enzyme I-SceI is introduced to the cell carrying the target gene locus (SexA1 site), cells carrying the vector-inserted target construct are obtained from the hygromycin-resistant colonies by PCR screening, after culturing and seeding this clone, ganciclovir-resistant colonies are yielded, and gene-modified cells are obtained.

This way, to obtain cells carrying the vector-inserted target structure, which is the product of the first step of the methods of the present invention, a donor plasmid DNA carrying a single DNA cleavage site on the 5' side in the post-modification nucleotide sequence and carrying a positive selection marker gene and a negative selection marker (exclusion marker) gene in the backbone region of the plasmid (see FIG. 1A), or a donor plasmid DNA carrying a single DNA cleavage site on the 3' side in the post-modification nucleotide sequence and carrying a positive selection marker gene and a negative selection marker gene in the backbone region of the plasmid (see FIG. 2A) can be used on the pre-modification nucleotide sequence site. Here, the 5' side and the 3' side refer to the 5' side and the 3' side referred to in the sense strand of the gene subjected to modification, respectively.

Figure 3:
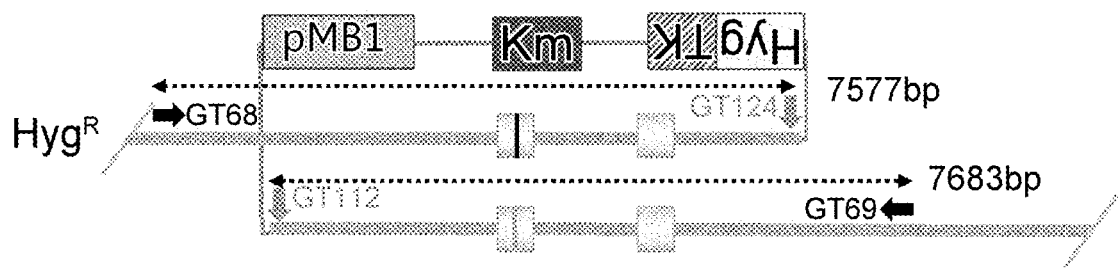
FIGS. 3A-B show a method for confirming the structure of a vector-inserted target construct.

FIG. 3 shows the method for performing PCR screening for the vector-inserted target construct. A shows the structure of the region subjected to vector target insertion. The post-modification sequence (synonymously converted sequence) derived from the donor plasmid is positioned downstream and the pre-modification sequence (SexA1 sequence) derived from the target gene locus is positioned upstream. As shown in the left panel of B, if a fragment corresponding to 7577 bp is detected with PCR using the genomic DNA of the cell targeted by the vector, the 5' external primer GT68 of the upstream 5488-bp fragment, and the primer GT124 of the HygTK promoter region positioned in the vector backbone, the fragment is deemed to be the structure of the upstream region (5' region) of the vector-inserted target construct. Similarly, as shown in the right panel of B, if a fragment corresponding to 7683 bp is detected with PCR using the primer GT112 of the pMB1 region located in the vector backbone and the 3' external primer GT68 of the downstream 5488-bp fragment, the fragment is deemed to be the structure of the downstream region (3' region) of the vector-inserted target construct. Furthermore, to confirm the co-existence of the SexA1 sequence of the upstream region and the synonymously converted sequence of the downstream region, a fragment corresponding to 525 bp is obtained with PCR using the GT19/GT22 primers for amplification of the exon 2 region where the molecular marker sequence is positioned, this fragment is subjected to sequence analysis, and from the yielded waveform chart, co-existence of two types of marker sequences is confirmed.

Figure 4:
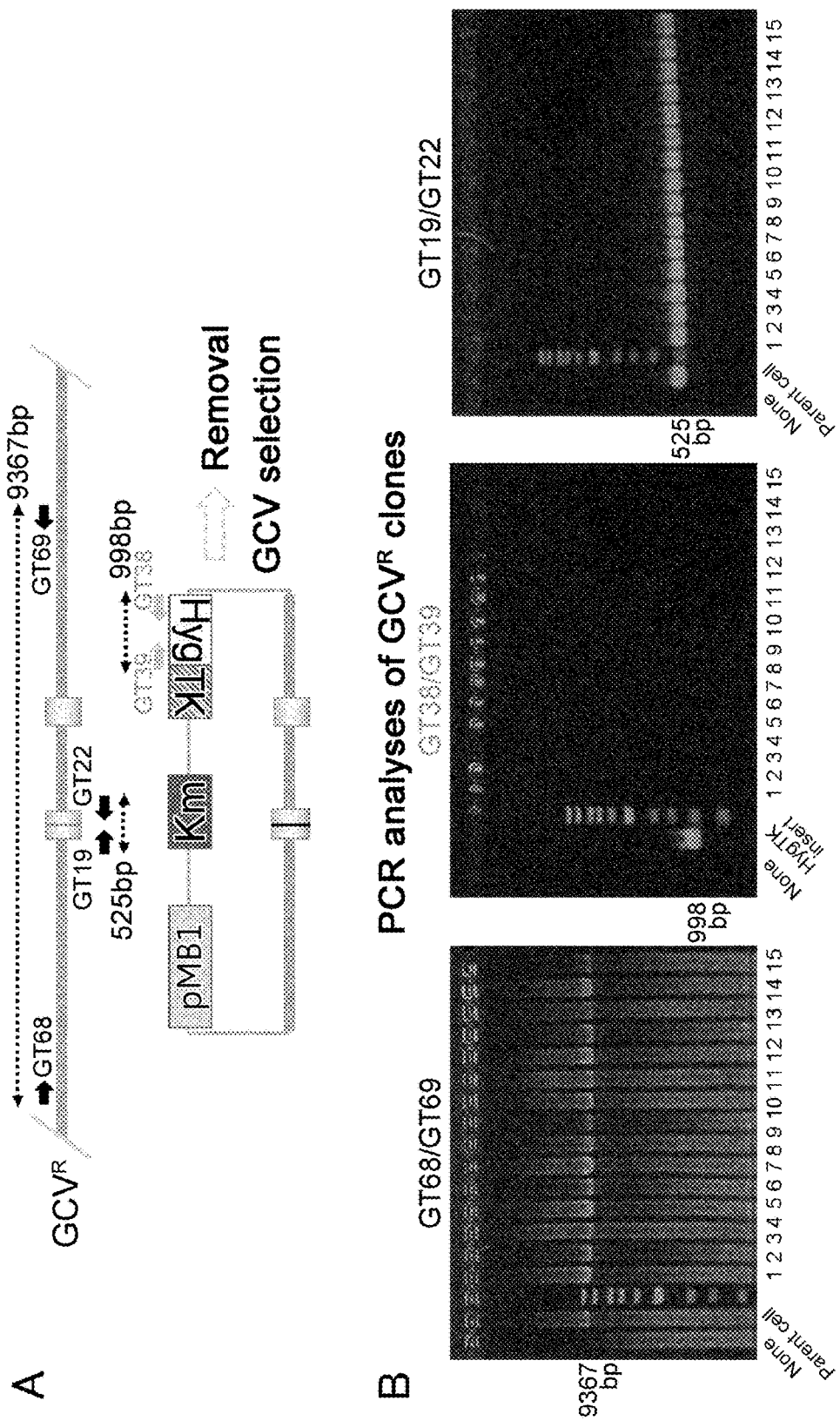
FIGS. 4A-B show a method for separating a gene variant by ganciclovir selection from one of the vector-inserted target constructs.

FIG. 4 shows the method for separating a gene variant from vector-inserted target constructs using ganciclovir selection. A shows that when replacement reaction from the vector-inserted target construct of FIG. 3A to the upstream (first half of the repeat) or downstream (latter half of the repeat) sequence takes place, this is accompanied by release of a vector plasmid carrying the downstream sequence or the upstream sequence, respectively. However, by ganciclovir selection, the cells carrying the released plasmid are removed, and candidate clones of the gene variants in which replacement reaction took place at the gene locus are obtained. As indicated in the left panel of B, to confirm that the gene locus of the ganciclovir-resistant clone has a replaced structure, PCR analysis is performed using the 5' external primer GT68 and the 3' external primer GT69 of the 5488 bp fragment of the homologous gene locus region, and if a fragment corresponding to 9367 bp is detected, this is deemed to be the structure of a modified gene. As indicated in the center panel of B, to confirm that a released plasmid does not exist in the cells of the ganciclovir-resistant clone, PCR analysis is performed using the GT38/GT39 primers which amplifies the Hyg region of the HygTK gene on the plasmid, and if a fragment corresponding to 998 bp is not produced, this cell clone is determined not to include a released plasmid. Finally, as indicated in the right panel of B, to isolate a gene variant from the ganciclovir-resistant clones, a fragment corresponding to 525 bp is obtained with PCR using the GT19/GT22 primers which amplifies a region of exon 2 where the molecular marker sequence is positioned, and the sequence of the fragment is determined. This panel shows that cell clones can be obtained, in which replacement to the post-modification sequence has taken place from the repeating pre-modification sequence (SexA1 sequence) and post-modification sequence (synonymously converted sequence) on the vector-inserted target region. Furthermore, not only the form in which cleavage of the donor plasmid takes place at the 3' side, but the form in which cleavage takes place at the 5' side may also be a form for carrying out the invention. Difference in length before and after the modification position in the overlapping region is not a concern. That is, the overlapping region before the modification position (5' side of the coding strand of the gene) may be longer than the overlapping region after the modification position (3' side), the overlapping region before the position may be shorter than the overlapping region after the position, or both regions may have the same length.

Figure 5:
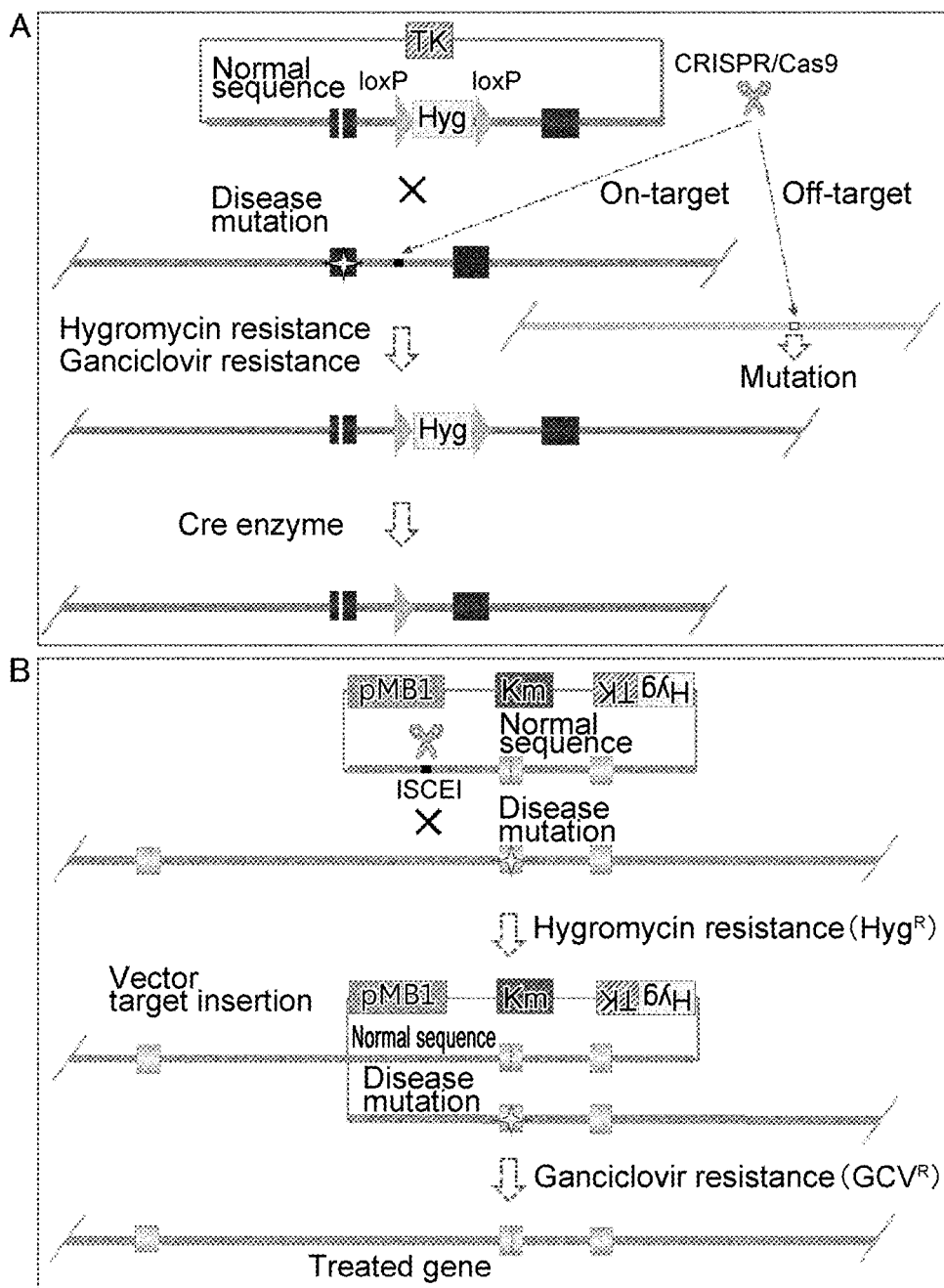
FIGS. 5A-C show methods for genetic modification: problems of the conventional methods and the superiority of the present invention.

FIG. 5 shows the problems of the conventional methods for genetic modification and the superiority of the method of the present invention. A depicts the problems to be solved by the invention. The column for "Problems" in C lists the above-mentioned problems to be solved such as the problem of On/Off-target inaccurate rejoining, the problem of residual site-specific recombination site, and the problem of loss of target cleavage sequence. B depicts the means for solving those problems. As shown in C, by using the method of the present invention, problems such as On/Off-target inaccurate rejoining, residual site-specific recombination site (loxP and such), and loss of target cleavage sequence can be avoided.

The present invention is useful for introducing desired modifications to the genome of cells, and for example, in a causative gene of a hereditary disease, the invention can be used to convert a disease-causing sequence to a normal sequence. As an example of the method for repairing disease mutations of the present invention, in the first step, a vector-inserted target structure is constructed in the target disease-causing gene, in which the linker polynucleotide (for example, the backbone region of a plasmid) in the donor polynucleotide is sandwiched between a normal nucleotide sequence that does not cause the hereditary disease subject to treatment and a disease-causing nucleotide sequence subject to treatment so that the normal nucleotide sequence and the disease-causing nucleotide sequence are arranged in tandem (in no particular order), and in the second step, the target disease-causing nucleotide sequence is converted to the normal nucleotide sequence by replacement to a single structure having only the normal nucleotide sequence spontaneously from the vector-inserted target structure.

An example of a donor polynucleotide used for repairing disease mutations is a donor polynucleotide carrying a single DNA cleavage site in the normal nucleotide sequence on the 5' side of the disease-causing nucleotide sequence site (5' side in the sense strand of the gene) and carrying a selection marker (positive selection marker) gene and an exclusion marker (negative selection marker) gene in the linker polynucleotide (for example, the backbone region of a plasmid) of the donor polynucleotide (see FIG. 1A), or a donor polynucleotide carrying a single DNA cleavage site in the normal nucleotide sequence on the 3' side of the disease-causing nucleotide sequence site (3' side in the sense strand of the gene) and carrying a selection marker gene and an exclusion marker gene in the linker polynucleotide (for example, the backbone region of a plasmid) (see FIG. 2A), for obtaining cells carrying the vector-inserted target structure, which is the product of the first step of the above-mentioned methods for repairing disease mutations.

Introducing this donor polynucleotide into cells carrying a disease mutation yields cells carrying the disease mutation-repairing vector-inserted target construct. These cells are cell strains carrying a vector-inserted target structure, in which the disease-causing nucleotide sequence is spontaneously replaced into the normal nucleotide sequence to thereby convert the vector-inserted target structure, which is the product of the first step of the aforementioned method for repairing disease mutations, to a single structure having only the normal nucleotide sequence. More specifically, this cell strain concerns a cell having on its chromosome a vector-inserted target structure in which the linker polynucleotide (for example, the backbone region of a plasmid) in the donor polynucleotide is sandwiched between the normal nucleotide sequence which does not cause the hereditary disease subject to treatment and the disease-causing nucleotide sequence subject to treatment so that they are tandemly arranged in no particular order (that is in any order). In this cell strain, this vector-inserted target structure is spontaneously and stochastically replaced into a single structure having only the normal nucleotide sequence.

Furthermore, the present invention provides a single locus substitution method that uses the donor polynucleotide of the present invention. Even when a hereditary disease is a monogenic disease, there is diversity in mutation regarding the sequence, structure, and size. To substitute the gene locus using one donor polynucleotide for each of such various disease mutations, the donor polynucleotide of the present invention is enlarged to several tens of kb or several hundreds of kb so that it corresponds to the size of a single gene locus. This provides a method for repairing a gene, wherein in the first step, a vector-inserted target structure is constructed in the target disease-causing gene locus, in which the linker polynucleotide (for example, the plasmid backbone region) in the donor polynucleotide is sandwiched between the normal gene locus which does not develop the hereditary disease subject to treatment and the single locus of the disease-causing mutation subject to treatment, so that the normal gene locus and the disease-causing mutant gene locus are tandemly arranged (in no particular order), and in the second step, the target disease-causing mutant gene locus is converted to the normal gene locus by spontaneous replacement of the vector-inserted target structure to a single structure having only the normal gene locus.

The present invention also relates to a donor polynucleotide for single locus substitution used in the single locus substitution method described above. Specifically, the donor polynucleotide is a donor polynucleotide carrying a single DNA cleavage site on the 5' side of a normal gene locus with respect to the disease-causing mutation site and carrying a selection marker gene and an exclusion marker gene in the linker polynucleotide (for example, the backbone region of a plasmid), which is a donor polynucleotide of the same type but larger in size compared with the aforementioned donor polynucleotide used to repair disease mutations (see FIG. 1A), or a donor polynucleotide carrying a single DNA cleavage site on the 3' side of a normal gene locus and carrying a selection marker gene and an exclusion marker gene in the linker polynucleotide (for example, the backbone region of a plasmid) (see FIG. 2A), for obtaining cells carrying the vector-inserted target structure, which is the product of the first step of the above-mentioned single locus substitution method.

By introducing this donor polynucleotide to cells subjected to single locus substitution, cells carrying the single locus-substituting vector-inserted target construct can be obtained. These cells are cell strains carrying a vector-inserted target structure of the same type but larger in size compared with the vector-inserted target structure which is the product of the first step of the aforementioned disease mutation-repairing method, in which cells the disease-causing mutant gene locus is spontaneously replaced to the normal gene locus to thereby convert the vector-inserted target structure, which is the product of the first step of the aforementioned single locus substitution method to a single structure having only the normal gene locus.

Furthermore, the present invention is also useful for shortening the step for obtaining cells having a single structure, by introducing a donor polynucleotide to target cells and via cells carrying the target-inserted construct of the donor polypeptide. Specifically, for example, if the donor polynucleotide has a plasmid vector backbone, during selective culturing of cells of a cell population in which the plasmid DNA is inserted into the genome or is freely present dissociated from the genome, when cells carrying the vector-inserted target structure at the target region contained in the cell population are spontaneously replaced and cells carrying a single structure composed of the upstream or downstream are produced, cells that have undergone random genome insertion of a released donor plasmid DNA (for example, cells in which the donor plasmid DNA sequence has been inserted at a position that is not the site of the target gene) are subjected to negative selective culturing, cells having the single structure are selected, and clones comprising the post-modification sequence may be selected.

A donor polynucleotide of the present invention may be appropriately made into a composition together with a pharmaceutically acceptable carrier or medium. A composition containing a donor polynucleotide of the present invention is used as a pharmaceutical composition, for example, a pharmaceutical composition for genome repair of a genetic disease. The carrier and medium are not particularly limited, and examples include water (for example, sterilized water), physiological saline solution (for example, phosphate buffered physiological saline solution), ethanol, glycerol, lactose, sucrose, calcium phosphate, gelatin, dextran, agar, pectin, peanut oil, and sesame oil, and other examples include buffers, double diluents, excipients, and adjuvants.

The administration route may be determined appropriately, and is not particularly limited. The donor polynucleotide or the composition of the present invention can be used in vitro or ex vivo, and for example, it can be administered by intramuscular injection, intravenously, percutaneously, intranasally, intraperitoneally, orally, mucosally, or by other delivery routes. The number of administrations and dose are not limited, and it may be a single use or multiple administrations. Those skilled in the art can make appropriate selections according to the type of composition, target cell, subject of administration, symptom and condition of tissue, disease, and subject to be treated, administration route, administration method, and such. Examples of the subject of administration include mammalian animals (including humans and non-human mammals), and specifically include humans, non-human primates such as monkeys, rodents such as mice and rats, rabbits, goats, sheep, pigs, cattle, dogs, cats, and all other mammalian animals.

Furthermore, the present invention relates to kits containing a donor polynucleotide of the present invention. The kits may contain a donor polynucleotide of the present invention, and a cleavage enzyme which cleaves the cleavable site of the genomic fragment in the donor polynucleotide or a vector encoding the enzyme. Furthermore, an instruction manual can be suitably added to the kits. Kits of the present invention are useful in genome modification using a donor polynucleotide of the present invention.

As the vector, a desired vector may be used, and examples include plasmid vectors and viral vectors. Examples of the viral vectors include minus strand RNA virus vectors, particularly paramyxovirus vectors, and especially Sendai virus vectors.

EXAMPLE

Herein below, the present invention will be specifically described with reference to Examples, but it is not to be construed as being limited thereto. All documents and other references cited herein are incorporated as part of this description.

[Example 1] Production of Donor Polynucleotides

Construction of pMB1KmHygTK-HPRTEx2Syn(1200)ISCEI (see FIG. 2A)

A method for producing a donor plasmid vector used in the Examples is shown below.

In the present invention, "pMB1KmHygTK" indicates the donor plasmid vector backbone. The expression "pMB1" in the vector backbone indicates the region necessary for initiating *E. coli* DNA replication, "Km" indicates the kanamycin resistance gene which is an *E. coli* selection marker, and "HygTK" indicates the fusion gene comprising the hygromycin resistance gene (animal cell selection marker) and HSV-TK (animal cell exclusion marker) which are under the control of the hEF1-HTLV promoter which is one of the human transcription initiation regions.

The sequence homologous to the gene locus to be modified which contains the post-modification sequence inserted to the vector backbone is indicated following the hyphen after the vector backbone, and is expressed as "-HPRTEx2Syn(1200)ISCEI". The expression "HPRTEx2" indicates the fragment covering intron 1, exon 2, intron 2, exon 3, and intron 3 of the human HPRT gene, furthermore, the expression "Ex2Syn" indicates that the post-modification sequence Syn is included in Ex2, and the expression "(1200)ISCEI" indicates that the I-SceI cleavage enzyme recognition sequence is positioned 1200 bp to the 3' side from the post-modification sequence Syn. In other examples, the sequence homologous to the gene locus to be modified which contains the post-modification sequence inserted to the vector backbone is indicated following the hyphen after the vector backbone, and is expressed as "-HPRTISCEI(1200)Ex2Syn". The expression "Ex2Syn" indicates that the post-modification sequence Syn is included in Ex2, and "ISCEI (1200)" indicates that the I-SceI cleavage enzyme recognition sequence is positioned 1200 bp to the 5' side from the post-modification sequence Syn.

However, the above is only an example, and the present invention is not limited thereto.

Construction of the pMB1KmHygTK donor plasmid (see FIG. 2A)

Construction of the pSelect-Km-HSV1tk subplasmid was carried out as follows. With pCR-BluntII-TOPO plasmid DNA (Invitrogen) as a template, and using 5'-CTTAAT-TAACCTGCAGCCGGAATTGCCAGCTG-3' (GT82) (SEQ ID NO: 2) and 5'-ATGTGGTATGGAAT-TCGGTGGCCCTCCTCACGTGC-3' (GT83) (SEQ ID NO: 3), PCR reaction using KOD-PLUS DNA polymerase (TOYOBO) (94° C. for 2 minutes→40 cycles of 94° C. for 15 seconds, 55° C. for 30 seconds, and 68° C. for 1 minute 30 seconds→68° C. for 7 minutes) was performed to obtain an approximately 1000-base PCR product. The above-mentioned 1000-base PCR product, and pSelect-ZEO-HSV1tk digested using the EcoRI restriction enzyme and the PstI restriction enzyme were linked using an In-Fusion kit (TOYOBO) to obtain pSelect-Km-HSV1tk (1).

Construction of the pSelect-ZEO-HygTK subplasmid was performed as follows. pSelect-ZEO-HSV1tk was digested using NcoI and SphI, and by treatment with T4 DNA polymerase in the presence of dNTPs, the cleaved ends were smoothed. On the other hand, with pcDNA3.1/Hygro as a template, and using 5'-TCACCGGTCACCAT-GAAAAAGCCTGAACTCACCGCG-3' (GT38) (SEQ ID NO: 4) and 5'-TCAAAGGCAGAAGCAACTTCTA-CACAGCCATCGGTCC-3' (GT39) (SEQ ID NO: 5), PCR reaction using KOD-PLUS DNA polymerase (TOYOBO) (94° C. for 2 minutes→40 cycles of 94° C. for 15 seconds, 58° C. for 30 seconds, and 68° C. for 1 minute 30 seconds→ and 68° C. for 7 minutes) was performed to obtain an approximately 1000-base PCR product. The above-mentioned smoothed pSelect-ZEO-HSV1tk and the 1000-base PCR product were linked using an In-Fusion kit (TOYOBO) to obtain pSelect-ZEO-HygTK (28-10).

Construction of the pMB1KmHygTK donor plasmid was performed as follows. With pSelect-ZEO-HygTK (28-10) as a template, and using 5'-ATTTAAATCAGCGGCCGCG-GATCTGCGATCGCTCCG-3' (GT84) (SEQ ID NO: 6) and 5'-TGTCTGGCCAGCTAGCTCAGGTTTAGTTGGCC-3' (GT85) (SEQ ID NO: 7), PCR reaction using KOD-PLUS-DNA polymerase (TOYOBO) (94° C. for 2 minutes→40 cycles of 94° C. for 15 seconds, 58° C. for 30 seconds, and 68° C. for 3 minutes→68° C. for 7 minutes) was performed to obtain an approximately 2800-base PCR product. The above-mentioned 2800-bp PCR product, and pSelect-Km-HSV1tk (1) digested using NotI and NheI were linked using an In-Fusion kit (TOYOBO) to obtain pMB1KmHygTK (1). Hereafter, this plasmid was used as the donor plasmid vector.

Construction of the pBS-HPRTEx2Syn(1200)ISCEI Subplasmid

Methods for constructing subplasmids for the production of a donor plasmid vector used in the present invention are shown below. In the present invention, "pBS" indicates pBluescript SK+.

Construction of the pBS-HPRTEx2 subplasmid was carried out as follows. With the genomic DNA of fibrosarcoma-derived HT-1080 cell as a template, and using 5'-AGCCTGGGCAACATAGCGAGACTTC-3' (GT28) (SEQ ID NO: 8) and 5'-TCTGGTCCCTACAGAGTCC-CACTATACC-3' (GT22) (SEQ ID NO: 9), PCR reaction using KOD-PLUS-DNA polymerase (TOYOBO) (94° C. for 2 minutes→40 cycles of 94° C. for 15 seconds, 60° C. for 30 seconds, and 68° C. for 3 minutes 30 seconds→68° C. for 7 minutes) was performed to obtain an approximately 2800-base PCR product. With the genomic DNA of fibrosarcoma-derived HT-1080 cell as a template, and using 5'-GCTGG-GATTACACGTGTGAACCAACC-3' (GT19) (SEQ ID NO: 10) and 5'-TGGCTGCCCAATCACCTACAGGATTG-3' (GT24) (SEQ ID NO: 11), PCR reaction using KOD-PLUS-DNA polymerase (94° C. for 2 minutes→40 cycles of 94° C. for 15 seconds, 58° C. for 30 seconds, and 68° C. for 8 minutes→68° C. for 7 minutes) was performed to obtain an approximately 3100-base PCR product. With the above-mentioned 2800-bp PCR product and the 3100-bp PCR product as templates, and using 5'-ATC-CACTAGTTCTAGAAGCCTGGGCAACATAGCGA-GACTTC-3' (GT29) (SEQ ID NO: 12) and 5'-CACCGCGGTGGCGGCCGCTGGCTGCCCAAT- CACCTACAGGATTG-3' (GT30) (SEQ ID NO: 13), PCR reaction using KOD-PLUS-DNA polymerase (TOYOBO CO., LTD. code number KOD-101) (94° C. for 2 minutes→40 cycles of 94° C. for 15 seconds, 58° C. for 30 seconds, and 68° C. for 6 minutes→68° C. for 7 minutes) was performed to obtain an approximately 5500-base PCR product. The above-mentioned 5500-bp PCR product and pBluescript SK+ digested with NotI were linked using an In-Fusion kit (Clontech Laboratories, Inc. catalog number 639649) to obtain pBS-HPRTEx2(18-7). Hereafter, this plasmid was used as a template for site-directed mutagenesis.

Construction of the pBS-HPRTEx2ISCEI subplasmid was performed as follows. With the genomic DNA of fibrosarcoma-derived HT-1080 cell as a template, and using 5'-TAGTTCTAGAGCGGCCGCAGCCTGGGCAACAT-AGCGAGACTTC-3' (GT35) (SEQ ID NO: 14) and 5'-AT-TACCCTGTTATCCCTAACCTGGTTCATCAT-CACTAATCTG-3' (GT34) (SEQ ID NO: 15) containing the I-SceI recognition sequence (underlined), PCR reaction using KOD-PLUS-DNA polymerase (TOYOBO CO., LTD. code number KOD-101) (94° C. for 2 minutes→40 cycles of 94° C. for 15 seconds, 58° C. for 30 seconds, and 68° C. for 3 minutes→68° C. for 7 minutes) was performed to obtain an approximately 2500-base PCR product. With the genomic DNA of fibrosarcoma-derived HT-1080 cell as a template, and using 5'-TAGGGATAACAGGGTAAT-TATGACCTTGATTTATTTTGCATACC-3' (GT33) (SEQ ID NO: 16) containing the I-SceI recognition sequence (underlined) and 5'-CACCGCGGTGGCGGCCGCTGGCTGCCCAAT-CACCTACAGGATTG-3' (GT30) (SEQ ID NO: 13), PCR reaction using KOD-PLUS-DNA polymerase (94° C. for 2 minutes→40 cycles of 94° C. for 15 seconds, 58° C. for 30 seconds, and 68° C. for 3 minutes→68° C. for 7 minutes) was performed to obtain an approximately 2900-base PCR product. The above-mentioned 2500-bp PCR product and 2900-bp PCR product, and pBluescript SK+ digested with NotI were linked using an In-Fusion kit (TOYOBO) to obtain pBS-HPRTEx2ISCEI (21-1). Hereafter, this plasmid was used as a plasmid receiving as a substituent fragment a modified sequence-carrying fragment obtained by site-directed mutagenesis.

Construction of the pBS-HPRTEx2Syn subplasmid was performed as follows. With pBS-HPRTEx2(18-7) as a template, and using 5'-GGCTACGATCTCGACCTCTTTTG-CATACCTAATCATTATGC-3' (GT93) (SEQ ID NO: 17) containing the post-modification sequence Syn (underlined) and 5'-TGGTTCATCATCACTAATCTG-3' (GT95) (SEQ ID NO: 18), pBS-HPRTEx2Syn(Inv15) was obtained using a KOD-PLUS-Inverse PCR mutagenesis kit (TOYOBO) as one method of site-directed mutagenesis. The BglII-SphI fragment containing the Syn sequence obtained by BglII and SphI digestion and gel extraction of the pBS-HPRTEx2Syn (Inv15) plasmid DNA, and the BglII- and SphI-digested HPRTEx2ISCEI (21-1) plasmid DNA sample were ligated to obtain pBS-HPRTEx2Syn(Inv15-2).

Construction of the pBS-HPRTEx2Syn(1200)ISCEI subplasmid was carried out as follows. With pBS-HPRTEx2Syn (Inv15-2) as a template, and using 5'-TAGGGA-TAACAGGGTAATATTTTGTAGAAACAGGGTTCGC-3' (GT86) (SEQ ID NO: 19) containing the ISCEI sequence (underlined) and 5'-AAAAATATTAGCTGGGAGTGG-3' (GT87) (SEQ ID NO: 20), pBS-HPRTEx2Syn(1200)ISCEI (1) was obtained by using a KOD-PLUS-Inverse PCR mutagenesis kit (TOYOBO).

Construction of the pMB1KmHygTK-HPRTEx2Syn (1200)ISCEI donor plasmid vector was carried out as follows. The NotI-digested pBS-HPRTEx2Syn(1200)ISCEI (1) DNA sample, and the NotI-digested pMB1 KmHygTK plasmid DNA were ligated to obtain pMB1KmHygTK-HPRTEx2Syn(1200)ISCEI (5), and the direction of insertion was confirmed to be the same as that shown in FIG. 2A.

[Example 2] Gene Modification Using a Donor Polynucleotide (1)

Production of the HTG786 cells carrying the vector-inserted target construct (see FIG. 2B and FIG. 3AB) was performed as follows. On the day before electroporation, $3 \times 10^6$ fibrosarcoma-derived HT-1080 cells were applied to six T75 flasks each containing 10 mL of DMEM medium to perform adhesive culturing; the medium was removed approximately 24 hours later: addition and removal of 5 mL of PBS was performed in each T75 flask: 2 mL of a 0.25% trypsin/1 mM EDTA solution was added to each T75 flask; incubation was performed at 37° C. for one minute: 3 mL DMEM medium was added to each T75 flask, the cells were detached and suspended by pipetting (using a pipette for 10 mL) three to four times, and these were collected into a single 50-mL tube which was centrifuged at 1,200 rpm for three minutes and the supernatant was removed; 20 mL of Opti-MEM was added and pipetting (using a pipette for 10 mL) was performed to suspend the cells, the cell count was determined, and then this was centrifuged again at 1.2000 rpm for three minutes and the supernatant was removed; Opti-MEM was added to yield $1 \times 10^7$ to $2 \times 10^7$ cells/mL; a P1000 pipette was set to 800 μL and pipetting was repeated 10 to 20 times slowly to avoid bubbles; 10 μg of pMB1KmHygTK-HPRTEx2Syn(1200)ISCEI donor plasmid vector DNA (500-1000 μg/mL endotoxin-free TE) and 13.3 μg of the plasmid DNA for pISceI expression (Nature vol. 401 pp 397; 500-1000 μg/mL endotoxin-free TE) were introduced to a 1.5-mL Eppendorf tube, and 0.8 mL of the cell suspension was introduced and mixed with the DNA solution; the entire amount of the mixed cell-DNA solution was transferred to a cuvette for electroporation (4 mm between electrodes), and this was left to stand in ice for five minutes; a BTX electroporator was set to 140 mV, pulse length of 70 mS, three pulses, and pulse interval of 200 mS; the cuvette was placed into the electroporation apparatus and voltage was applied: the cuvette was removed from the apparatus and was left to stand in ice for five minutes: the entire amount of the electroporation solution was transferred into 165 mL of DMEM medium not containing the selection reagent, this was mixed slowly, and then applied to 16 10-cm diameter dishes at 10 mL per dish; and non-selective culturing was started at 37° C. under conditions of 5% $CO_2$ (Day 0). On Day 2, the medium was exchanged to a DMEM medium containing 100 μg/mL hygromycin, and selective culturing was started; medium exchange was performed every two or three days using the same selection medium; on Day 14, the number of hygromycin-resistant colonies were determined from four representative dishes; the medium was exchanged to a DMEM medium containing 100 μg/mL hygromycin and 7.5 μg/mL 6-thioguanine to initiate double selective culturing: medium exchange was performed every two or three days using the same selection medium; and on Day 21, the number of hygromycin and 6-thioguanine double-resistant (HTG) colonies on all of the dishes was determined.

As a result of the above-mentioned experiment, 6472 hygromycin-resistant colonies were obtained under hygromycin selection, and 14 HTG clones were obtained under hygromycin and 6-thioguanine double selection.

The procedure for isolating the vector-inserted target constructs (see FIG. 2DE; and see FIG. 3AB) was performed as follows. For each of the HTG colonies, under microscope observation, a P1000 Pipetman set to 200 µL was used to detach the cells, and this was suspended in a single well of a 6-well plate to which 2 mL of DMEM containing 100 µg/mL hygromycin and 7.5 µg/mL 6-thioguanine was added, HTG clone number was assigned, and the cells were selectively cultured under conditions of 37° C. and 5% $CO_2$, and culturing was continued until nearly confluent. The medium was removed; addition and removal of PBS was carried out at 2 mL/well: a 0.25% trypsin/1 mM EDTA solution was added at 500 µL/well, and this was incubated at 37° C. for one minute: a DMEM medium was added at 500 µL/well, and by pipetting three to four times using P1000, cells were detached and suspended; cells were collected in a single 1.5-mL Eppendorf tube, this was centrifuged at 2,500 rpm for three minutes and the supernatant was removed; 100 µL of PBS was added and the cells were suspended by pipetting, this was separated into two cryotubes at 40 µL per tube, 500 µL of CELLBANKER 1 plus was added per cryotube, the tubes were stored at −80° C., and the remaining 20 µL of PBS cell suspension was centrifuged at 2,500 rpm for three minutes, the supernatant was removed, and the resulting cell pellet was frozen and stored at −80° C. The frozen cell pellet was thawed in ice, the genomic DNA was extracted using a GeneElute Mammalian Genomic DNA miniprep Kit (SIGMA-ALDRICH, catalog number GIN350), and this was stored at 4° C. as 100-µL samples. With the genomic DNA of the HTG clone as a template, and using 5'-TTGCAAGCAGCAGATTACGC-3' (GT112) (SEQ ID NO: 21) and 5'-GCCACTGCACCCAGCCGTATGT-3' (GT69) (SEQ ID NO: 22), PCR reaction using KOD-FX-DNA polymerase (TOYOBO) (94° C. for 2 minutes→40 cycles of 98° C. for 10 seconds and 68° C. for 8 minutes→68° C. for 7 minutes) was performed to determine that the HTG clone which yielded the approximately 7700-base PCR product in a similar manner to the right side of FIG. 2B is a cell carrying the vector-inserted target construct having the structure of FIG. 2A.

As a result of the above-mentioned experiment, eight cells carrying the vector-inserted target construct were obtained from 14 HTG clones. This implies that among all of the 6472 clones of the vector genome-inserted constructs, which are a combination of constructs with random insertion and targeted insertion of the vector, eight clones were the vector-inserted target constructs. Therefore, the practicality of acquiring target-inserted constructs is $1.2 \times 10^{-3}$, and this suggests that the target-inserted construct of interest can be obtained from 1000 vector genome-inserted clones.

As indicated in FIG. 3 and its description herein, when sequence analyses were performed to investigate whether the two marker sequences, which are the pre-modification sequence (SexA1 sequence) and the post-modification sequence (synonymously converted sequence Syn), coexist in the vector-inserted target construct, that is, whether they exist as heterotypes, among the eight vector-inserted target clones, one was a SexA1 homotype, but the other seven including HTG786 were heterotypes or Syn homotypes. The heterotype and Syn homotype vector-inserted target constructs can advance to the step of isolating the gene-substituted construct (described in the next paragraph).

The procedure for isolating a gene-substituted construct carrying a sequence after genetic modification from vector-inserted target constructs (see FIG. 4AB) was performed as follows. HTG786 cells belonging to one of the eight vector-inserted target clones were used. Cells of this clone stored at −80° C. was thawed using a 37° C. water bath, this was transferred to a 50-mL tube containing 9 mL of DMEM medium, and then centrifuged at 1,200 rpm for 3 minutes, the supernatant was removed, 10 mL of DMEM medium was added and pipetted to suspend the cells, and this was subjected to adhesive culturing in a T75 flask at 37° C. under 5% $CO_2$. Approximately 24 hours later, the medium was removed; addition and removal of PBS was performed at 10 mL in each T75 flask; 1 mL of a 0.25% trypsin/1 mM EDTA solution was added to each T75 flask; incubation was performed at 37° C. for one minute; 9 mL of DMEM medium was added to each T75 flask, the cells were detached and suspended by pipetting (using a pipette for 10 mL) three to four times, and these were collected into a 50-mL tube; after determining the cell count, this was centrifuged at 1,200 rpm for three minutes, and the supernatant was removed; DMEM medium was added to yield $2 \times 10^5$ cells/mL; and 50 µL of this cell suspension ($1 \times 10^4$ cells) was spread onto a 10-cm dish containing 10 mL of DMEM medium, and adhesive culturing at 37° C. under 5% $CO_2$ was started (Day 0). On Day 5, the medium was exchanged to a DMEM medium containing 1 µM ganciclovir (InvivoGen, catalog number #sud-gcv) and selective culturing was started. On Days 7, 9, and 12, the medium was exchanged; on Days 20 to 25, the number of ganciclovir-resistant (GCV) colonies were counted; for each of the GCV colonies, under microscope observation, a P1000 Pipetman set to 200 µL was used to detach the cells, and this was suspended in a single well of a 6-well plate to which 2 mL of DMEM containing 1 µM ganciclovir was added, GCV clone number was assigned, and the cells were selectively cultured under conditions of 37° C. and 5% $CO_2$, and culturing was continued until confluent. The medium was removed; addition and removal of 2 mL of PBS/well was carried out; a 0.25% trypsin/1 mM EDTA solution was added at 500 µL/well, and this was incubated at 37° C. for one minute; a DMEM medium was added at 500 µL/well, and by pipetting three to four times using P1000, cells were detached and suspended; cells were collected in a single 1.5-mL Eppendorf tube, this was centrifuged at 2,500 rpm for three minutes and the supernatant was removed; 100 µL of PBS was added and the cells were suspended by pipetting, this was separated into two cryotubes at 40 µL per tube, 500 µL of CELLBANKER 1 plus was added per cryotube, the tubes were stored at −80° C., and the remaining 20 µL of PBS cell suspension was centrifuged at 2,500 rpm for three minutes, the supernatant was removed, and the resulting cell pellet was frozen and stored at −80° C. The frozen cell pellet was thawed in ice, the genomic DNA was extracted using a GeneElute Mammalian Genomic DNA miniprep Kit (SIGMA-ALDRICH, catalog number GIN350), and this was stored at 4° C. as 100-µL samples. With the genomic DNA of the GCV clone as a template, and using 5'-GCTGG-GATTACACGTGTGAACCAACC-3' (GT19) (SEQ ID NO: 10) and 5'-TCTGGTCCCTACAGAGTCCCAC-TATACC-3' (GT22) (SEQ ID NO: 9), PCR reaction using KOD-FX-DNA polymerase (TOYOBO CO., LTD. code number KFX-101) (94° C. for 2 minutes→40 cycles of 98° C. for 10 seconds and 68° C. for 1 minute→68° C. for 7 minutes) was performed, an approximately 500-base PCR product was confirmed in a similar manner to FIG. 4C, and after purification using PCR clean-up (MACHEREY-NAGEL, 740609.250), sequencing was performed.

As a result of the above-mentioned experiment, twelve GCV clones were obtained, and the clones in which the pre-modification sequence SEXA1 (5'-CCAGGT-TATGACCTTGATTTATTTT-3') (SEQ ID NO: 23) has been changed on exon 2 to the post-modification sequence Syn (underlined) (5'-CC<u>AGGCTACGATCTCGACCTCTTTT</u>-3') (SEQ ID NO: 24) derived from the pMB1KmHygTK-HPRTEx2Syn(1200)ISCEI donor plasmid vector were obtained.

(2)

A gene-substituted construct carrying a sequence after genetic modification was isolated again from the vector-inserted target construct HTG786. Twelve GCV-resistant colonies obtained from the experiment described in the previous paragraph (Experiment 1), and nine GCV-resistant colonies obtained from a similar experiment (Experiment 2) were individually subjected to limiting dilution at 5 cells per well (96-well plate), then cultured, and the clones were purified. As in the procedure described in the previous paragraph, with genomic DNA of the clone as a template, and using 5'-GCTGGGATTACACGTGTGAACCAACC-3' (GT19) (SEQ ID NO: 10) and 5'-TCTGGTCCCTA-CAGAGTCCCACTATACC-3' (GT22) (SEQ ID NO: 9), PCR reaction using KOD-FX-DNA polymerase (TOYOBO CO., LTD. code number KFX-101) (94° C. for 2 minutes→40 cycles of 98° C. for 10 seconds and 68° C. for 1 minute→68° C. for 7 minutes) was performed, an approximately 500-base PCR product was confirmed in a similar manner to FIG. 4C, and after purification using PCR clean-up (MACHEREY-NAGEL, 740609.250), sequencing was performed.

Based on the results of sequencing the GCV-resistant clones obtained from these two experiments, the clones were classified, and the results are summarized below.

TABLE 1

| | Collected GCV$^R$ colonies | SexA1 clones | Syn synonymously converted clones | Associated clones with random insertion |
|---|---|---|---|---|
| Experiment 1 | 12 | 2 | 9 | 1 |
| Experiment 2 | 9 | 2 | 2 | 5 |

These results show that by collecting about ten GCV-resistant colonies as gene-substituted cell candidates, and purifying the clones, gene-substituted constructs having the intended design (in this examination, the Syn synonymously converted clones) can be obtained from the GCV-resistant clones.

To optimize the structure of the donor plasmid, three types of donor plasmid vectors were constructed, in which the distances between the synonymously converted sequence site and the position of ISCEI cleavage in the donor plasmids are different. As indicated in Example 1, the sequence homologous to the gene locus to be modified which contains the post-modification sequence inserted to the vector backbone is indicated following the hyphen after the vector backbone, and is expressed as "-HPRTISCEI(1200) Ex2Syn". The expression "Ex2Syn" indicates that the synonymously converted post-modification sequence Syn is included in Ex2, "ISCEI (1200)" indicates that the I-SceI cleavage enzyme recognition sequence is positioned 1200 bp to the 5' side from the post-modification sequence Syn.

1) Construction of the pBS-HPRTISCEI(1200)Ex2Syn subplasmid was carried out as follows. With pBS-HPRTEx2Syn(Inv15-2) as a template, and using 5'-<u>TAGG-GATAACAGGGTAAT</u>CAAAGCACTGGGATTA-CAAGTG-3' (GT117) (SEQ ID NO: 25) containing the ISCEI sequence (underlined) and 5'-GGAGGCTGA-GACAGGAGAGTTGC-3' (GT118) (SEQ ID NO: 26), pBS-HPRTISCEI(1200)Ex2Syn(3) was obtained using a KOD-PLUS-Inverse PCR mutagenesis kit (TOYOBO).

2) Construction of the pBS-HPRTISCEI(600)Ex2Syn subplasmid was performed as follows. With pBS-HPRTEx2Syn(Inv15-2) as a template, and using 5'-<u>TAGG-GATAACAGGGTAAT</u>CAAAGTGCTGGGATTACAGGC-3' (GT131) (SEQ ID NO: 27) containing the ISCEI sequence (underlined) and 5'-GGAGGCCGAGGCGGGTGGATCA-3' (GT132) (SEQ ID NO: 28), pBS-HPRTISCEI(600) Ex2Syn(4) was obtained using a KOD-PLUS-Inverse PCR mutagenesis kit (TOYOBO).

3) Construction of the pBS-HPRTISCEI(316)Ex2Syn subplasmid was performed as follows. With pBS-HPRTEx2Syn(Inv15-2) as a template, and using 5'-<u>TAGG-GATAACAGGGTAAT</u>TGTATTTTTAGTAGAGACGGG-3' (GT133) (SEQ ID NO: 29) containing the ISCEI sequence (underlined) and 5'-AAAAAATTAGCCGGGTGTGG-3' (GT134) (SEQ ID NO: 30), pBS-HPRTISCEI(316)Ex2Syn (2) was obtained using a KOD-PLUS-Inverse PCR mutagenesis kit (TOYOBO).

1) Construction of the pMB1KmHygTK-HPRTISCEI (1200)Ex2Syn donor plasmid vector was performed as follows. A NotI-digested pBS-HPRTISCEI(1200)Ex2Syn(3) DNA sample and a NotI-digested pMB1KmHygTK plasmid DNA were ligated to obtain pMB1KmHygTK-HPRTISCEI (1200)Ex2Syn(1), and the direction of insertion was confirmed to be the same as that of FIG. 2A.

2) Construction of the pMB1KmHygTK-HPRTISCEI (600)Ex2Syn donor plasmid vector was performed as follows. A NotI-digested pBS-HPRTISCEI(600)Ex2Syn(4) DNA sample and a NotI-digested pMB1KmHygTK plasmid DNA were ligated to obtain pMB1KmHygTK-HPRTISCEI (600)Ex2Syn(1), and the direction of insertion was confirmed to be the same as that of FIG. 2A.

3) Construction of the pMB1KmHygTK-HPRTISCEI (316)Ex2Syn donor plasmid vector was performed as follows. A NotI-digested pBS-HPRTISCEI(316)Ex2Syn(2) DNA sample and a NotI digested pMB1KmHygTK plasmid DNA were ligated to obtain pMB1 KmHygTK-HPRTISCEI (316)Ex2Syn(1), and the direction of insertion was confirmed to be the same as that of FIG. 2A.

[Example 3] Construction of an I-SceI-Loaded Sendai Virus Vector

To utilize the advantage of Sendai virus vectors, which is absence of risk of random insertion into the genome, and to introduce a Sendai virus vector loaded with the I-SceI sequence-specific cleavage enzyme gene into cells and express it, the I-SceI-loaded Sendai virus vector was constructed as follows.

For the gene of the I-SceI enzyme carrying a nuclear localization signal at the N terminus, Saccharomyces cerevisiae-extracted DNA was used as a template, and using 5'-GGATCCTGCAAAGATGGATAAAGCGGAATTAAT-TCCCGAGCCTCCAAAAAAGAAGAG AAAGGTCGAATTGGGTACCATGAAAAATAT-TAAAAAAAATCAAGTAATGAATCTGGGT CC-3' (SEQ ID NO: 31) and 5'-ATGCATTTATTTTAAAAAAGTTTCG-GATGAAATAGTATTAGGC-3' (SEQ ID NO: 32), PCR reaction using KOD-PLUS-DNA polymerase (94° C. for 1 minute→30 cycles of 94° C. for 15 seconds, 40° C. to 54°

C. gradient for 30 seconds, and 68° C. for 1 minute) was performed to obtain an approximately 800-base PCR product, and the pUC-nlsISceI plasmid was obtained. With this plasmid DNA as a template, and using 5'-GTCGACCCGGGCGGCCGCCATGGATAAAGCG-GAATTAATTCCCG-3' (GT40) (SEQ ID NO: 33) and 5'-CTAAAGGGAAGCGGCCGCTTATTT-TAAAAAAGTTTCGG-3' (GT41) (SEQ ID NO: 34), PCR reaction using KOD-PLUS-DNA polymerase (94° C. for 2 minutes→30 cycles of 94° C. for 15 seconds, 55° C. for 30 seconds, and 68° C. for 1 minute→68° C. for 7 minutes) was performed to obtain an approximately 800-base PCR product. This PCR product was linked with a NotI-digested pCI-neo using an In-Fusion kit (TOYOBO) to obtain pCI-neo-nlsISceI(29-2).

To load the nlsISceI sequence-specific cleavage enzyme gene derived from pCI-neo-nlsISceI(29-2) into the Sendai virus vector SeV, the first PCR divided the nlsISCEI sequence into two to yield the first PCR products, the second PCR used the 5' side and the 3' side of the first PCR products as templates, a third PCR product spanning the full length of the nlsISCEI nuclease sequence was obtained, and this was loaded onto a Sendai virus vector. In the first PCR, the nlsISCEI sequence is divided into two because there are three A-rich sequences (7A, 8A) in the nlsISCEI sequence, and on A-rich sequences, errors by the Sendai virus RNA-dependent RNA polymerase tend to occur in the process of producing Sendai virus vectors, and this division is for avoiding such error events. On the A-rich sequence site, a PCR primer was set, and each primer sequence was subjected to substitution of A/T with G/C under the limitation of choosing synonymous codons.

TABLE 2

Primers and Template DNAs for the First PCR

| F_Primer (SEQ ID NO:) | R_Primer (SEQ ID NO:) | Template DNA | PCR product # |
|---|---|---|---|
| NLS-I-SceIN_A36G_A78G_A81G_N (35) | NLS-I-SceI_A426G_C (36) | pCI-neo-nlsISceI (29-2) | 1 |
| NLS-I-SceIN_A426G_N (37) | NLS-I-SceI_EIS_Not1_C (38) | PCI-neo-nlsISceI (29-2) | 2 |

The primer pair in the upper row, Not1_NLS—I-SceIN_A36G_A78G_A81G_N (also named: NLS—I-SceIN_N1) (5'-CGAGCCTC-CAAAGAAGAAGAGAAAGGTCGAATTGGGTAC-CATGAAAAATATTAAGA AGAATCAAGTAAT-3') (SEQ ID NO: 35) and NLS—I-SceI_A426G_C (5'-GTTCGG-GATGGTTTTCTTGTTGTTAACG-3') (SEQ ID NO: 36), and a template DNA were used for PCR reaction using KOD-PLUS-Ver.2-DNA polymerase (TOYOBO CO., LTD. code number KOD-211) (94° C. for 2 minutes→30 cycles of 98° C. for 10 seconds, 55° C. for 30 seconds, and 68° C. for 1 minute→68° C. for 7 minutes) to obtain PCR product #1. The primer pair in the lower row, NLS—I-SceIN_A426G_N (5'-CGTTAACAACAAGAAAACCATCCCGAAC-3') (SEQ ID NO: 37), NLS—I-SceI_EIS_Not1_C (5°-ATATGCGGCCGCGATGAACTTT-CACCCTAAGTTTTTCTTACTACGGTTATTT-TAAAAAA GTTTCGGATG-3') (SEQ ID NO: 38), and a template DNA were used for PCR reaction using KOD-FX-DNA polymerase (TOYOBO CO., LTD. code number KFX-101) (94° C. for 2 minutes→30 cycles of 98° C. for 10 seconds and 68° C. for 1 minute→68° C. for 7 minutes) to obtain PCR product #2. After the sizes of the PCR products were confirmed by electrophoresis, they were purified using NucleoSpin™ Gel and PCR Clean-up (MACGEREY-NA-GEL, catalog number 740609.250/U0609C).

TABLE 3

Primers and Template DNAs for the Second PCR

| F_Primer (SEQ ID NO:) | R_Primer (SEQ ID NO:) | Template DNA | PCR product # |
|---|---|---|---|
| Not1_NLS-I-SceIN_A36G_N (39) | NLS-I-SceI_EIS_Not1_C (38) | PCR product # 1, 2 | — |

The Not1_NLS—I-SceIN_A36G_N primer which has in its 3' end the 29 5'-end nucleotides (underlined) of the Not1_NLS—I-SceIN_A36G_A78G_A81G_N (also named: NLS—I-SceIN_N1) primer (5'-ATATGCGGCCGCGACGCCACCATGGATAAAGCG-GAATTAATTCCCGAGCCTCCAAAG AAGAAGAGAAAGGTCG-3') (SEQ ID NO: 39) and NLS—I-SceI_EIS_Not1_C (SEQ ID NO: 38), and a template DNA were used for PCR reaction using KOD-FX-DNA polymerase (TOYOBO CO., LTD. code number KFX-101) (94° C. for 2 minutes→40 cycles of 98° C. for 10 seconds and 68° C. for 1 minute→68° C. for 7 minutes) to obtain the full length PCR product. After the size of the product was confirmed by electrophoresis, it was purified using NucleoSpin™ Gel and PCR Clean-up (MACGEREY-NAGEL, catalog number 740609.250/U0609C). The full-length nlsISceI fragment subjected to NotI digestion and gel extraction was ligated with the pSeV18+TS15/ΔF plasmid DNA subjected to NotI digestion and BAP treatment (DNA encoding the genome of a Sendai virus vector (WO2003/025570, WO2010/008054) which lacks the F gene, and carries the mutations M (G69E/T116A/A183S), HN (A262T/G264/K461G), P (D433A/R434A/K437A/L511F), and L (L1361C/L1558I/N1197S/K1795E)), the cloned nlsISceI nucleotide sequence was confirmed, and the pSeV18+nlsISceITS15/ΔF plasmid loaded with the full-length nlsISceI optimized for SeV was obtained. Using this plasmid DNA as a template, Sendai virus was reconstituted, and the nlsISceI-loaded Sendai virus vector SeV18+nlsIS-ceITS15/ΔF was obtained. The inserted sequence is shown below. The inserted sequence is the region sandwiched between the NotI site (underline)—sequence inserted for adjustment to the 6n rule (gac)—Kozak sequence (double underline) and the EIS sequence (wavy underline)—NotI site (underline). This sequence includes the nlsISceI (SEQ ID NO: 41)—coding sequence (positions 18 to 785 of SEQ ID NO: 40).

(SEQ ID NO: 40)
gcggccgcgacgccaccATGGATAAAGCGGAATTAATTCCCGAGCCTCC

CAAAgAAGAAGAGAAAGGTCGAATTGGGTACCATGAAAAATATTAAgAA gAATCAAGTAATGAATCTGGGTCCGAACTCTAAACTGCTGAAAGAATAC

AAATCCCAGCTGATCGAACTGAACATCGAACAGTTCGAAGCAGGTATCG

GTCTGATCCTGGGTGATGCTTACATCCGTTCTCGTGATGAAGGTAAAAC

CTACTGTATGCAGTTCGAGTGGAAAAACAAAGCATACATGGACCACGTA

TGTCTGCTGTACGATCAGTGGGTACTGTCCCCGCCGCACAAAAAAGAAC

-continued
GTGTTAACCACCTGGGTAACCTGGTAATCACCTGGGGCGCCCAGACTTT

CAAACACCAAGCTTTCAACAAACTGGCTAACCTGTTCATCGTTAACAAC

AAgAAAACCATCCCGAACAACCTGGTTGAAAACTACCTGACCCCGATGT

CTCTGGCATACTGGTTCATGGATGATGGTGGTAAATGGGATTACAACAA

AAACTCTACCAACAAATCGATCGTACTGAACACCCCAGTCTTTCCTTTC

GAAGAAGTAGAATACCTGGTTAAGGGTCTGCGTAACAAATTCCAACTGA

ACTGTTACGTAAAAATCAACAAAAACAAACCGATCATCTACATCGATTC

TATGTCTTACCTGATCTTCTACAACCTGATCAAACCGTACCTGATCCCG

CAGATGATGTACAAACTGCCTAATACTATTTCATCCGAAACTTTTTTAA

AATAAccgtagtaagaaaaacttagggtgaaagttcatcgcggccgc

[Example 4] Optimization of the Donor Plasmid Structure Regarding Vector Target Insertion of the Donor Polynucleotide During electroporation in the gene modification method using the donor polynucleotide shown in Example 2 (1), instead of the plasmid DNA for I-SceI expression (Nature vol. 401 pp 397), pCI-neo-nlsISceI(29-2)DNA (12.6 g) was used to produce vector-inserted target constructs by each of the three types of donor plasmids.

homologous region is 1960 bp or more, and the distance between the cleavage point and the designed sequence is 316 bp or more.

[Example 5] Vector Target Insertion of a Donor Polynucleotide Using an nlsISceI-Loaded Sendai Virus Vector On the day before infection with nlsISceI-loaded Sendai virus vector, HT-1080 cells were applied to a 6-well plate at $5 \times 10^5$ cells per 2 mL DMEM/10% FBS medium per well to perform adhesive culturing, the medium was removed approximately 24 hours later, 2 mL of Opti-MEM was added, and this was left to stand at 37° C.; meanwhile, the number of cells in a single well was measured and the total number of cells to be infected was calculated, nlsISceI-loaded Sendai virus vector SeV18+nlsISCEITS15/ΔF (Example 3) corresponding to multiplicity of infection of three was collected, adjustment to 0.5 mL SeV-nlsISceI solution/well was achieved by dilution with Opti-MEM, Opti-MEM which had been added in advance was removed, SeV-nlsISceI solution was added at 0.5 mL/well, adsorptive infection was initiated under conditions of 32° C. and 5% $CO_2$, mixing operation was carried out every 15 minutes, the SeV-nlsISCEI solution was removed two hours later, 2 mL of Opti-MEM was added per well, the medium was exchanged to 2 mL of DMEM medium (containing 6-thio-

TABLE 4

| ISceI-loaded vector | Left arm | Distance between cleavage point and synonymously converted sequence | Right arm | Total cell count | HYG$^R$ | Target inserted constructs | Heterotype or Syn homotype |
|---|---|---|---|---|---|---|---|
| pCI-neo | 1360 | ISCEI (1200) Syn | 2910 | 8.0e6 | 3516 | 0 | — |
| pCI-neo | 1360 | ISCEI (1200) Syn | 2910 | 8.0e6 | 1404 | 0 | — |
| pCI-neo | 1960 | ISCEI (600) Syn | 2910 | 8.0e6 | 1768 | 10 | 3 |
| pCI-neo | 1960 | ISCEI (600)Syn | 2910 | 8.0e6 | 1708 | 6 | 2 |
| pCI-neo | 1960 | ISCEI (600) Syn | 2910 | 5.0e6 | 2012 | 5 | 3 |
| pCI-neo | 2244 | ISCEI (316) Syn | 2910 | 8.0e6 | 4508 | 12 | 2 |
| pCI-neo | 2244 | ISCEI (316) Syn | 2910 | 8.0e6 | 4360 | 5 | 0 |
| pCI-neo | 2244 | ISCEI (316) Syn | 2910 | 1.6e7 | 7316 | 22 | 6 |
| pCI-neo | 2560 | Syn (1200) ISCEI | 1710 | 8.0e6 | 2932 | 4 | 2 |
| pCI-neo | 2560 | Syn (1200) ISCEI | 1710 | 8.0e6 | 11521 | 1 | 1 |
| pISceI | 2560 | Syn (1200) ISCEI | 1710 | 1.6e7 | 6472 | 8 | 7 | pCI-neo: pCI-neo-nlsISceI (29-4) plasmid
pISceI: plasmid for I-SceI expression (Nature vol. 401 pp397)
Left arm: length of the homologous region on the left side of the ISCEI cleavage site (bp) (see FIG. 1A); length of the homologous region on the left side of the Syn homologously converted sequence site (bp) (see FIG. 2A)
Right arm: length of the homologous region on the right side of the Syn homologously converted sequence site (bp) (see FIG. 1A); length of the homologous region on the right side of the ISCEI cleavage site (bp) (see FIG. 2A)

These examinations were performed using a DMEM/10% FBS medium as indicated in Example 2 (1). In the third experiment using the ISCEI (600) Syn-type donor plasmid, DMEM/2% FBS/1/100 vol. GlutaMAX-1 (100×) (gibco, product number 35050-061) was used as the medium. Under this low-FBS condition, selective culturing was performed using 50 μg/mL hygromycin and 0.94 μg/mL 6-thioguanine.

From these results, the length of the homologous region outside the cleavage point, the length of the homologous region outside the designed sequence, and the distance between the cleavage point and the designed sequence are not limited; however desirably, the length of the outside guanine) per well, and this was cultured under conditions of 32° C. and 5% $CO_2$. Approximately 24 hours later, the medium was exchanged to a fresh DMEM medium, this was transferred to 35° C. and 5% $CO_2$, and then cultured without further change for approximately 24 hours.

The subsequent cell collection, electroporation operation for introducing the donor plasmid described in the following table, application of cells, and non-selective culturing and selective culturing were performed similarly to Example 2 (1), and the operation for isolating the vector target constructs was also performed similarly to Example 2 (1).

TABLE 5

| ISceI-loaded vector | Left arm | Distance between cleavage point and synonymously converted sequence | Right arm | Total cell count | HYG$^R$ | Target inserted constructs | Heterotype or Syn homotype |
|---|---|---|---|---|---|---|---|
| SeV/TS15 | 1960 | ISCEI (600) Syn | 2910 | 8.0e6 | 2908 | 3 | 1 |
| SeV/TS15 | 1960 | ISCEI (600) Syn | 2910 | 8.0e6 | 1096 | 1 | 1 |

SeV/TS15: SeV18 + nlsISCEITS15/ΔF Sendai virus vector

Of the two examinations, the first examination was performed by following the above-mentioned conditions (using a DMEM/10% FBS medium, performing adsorptive infection of the Sendai virus vector at 32° C. for 24 hours and at 35° C. for 24 hours, and after applying the cells, non-selectively culturing at 37° C. for 3 days and selectively culturing at 37° C.). In the second examination, DMEM/2% FBS/1/100 vol. GlutaMAX-1 (100×) (gibco, product number 35050-061) was used as the medium, adsorptive infection of the Sendai virus vector was carried out at 32° C. for 48 hours, and after applying the cells, non-selective culturing at 35° C. for 3 days and selective culturing at 37° C. were carried out. Under this low-FBS condition, selective culturing was carried out using 50 μg/mL hygromycin and 0.94 μg/mL 6-thioguanine.

From these results, the cleavage enzyme gene expression vectors for intracellular cleavage are not limited to the plasmid type nor the virus vector type, but to avoid random insertion of the cleavage enzyme gene expression vector, the virus vector type is desirable.

[Example 6] Vector Target Insertion of a Donor Polynucleotide Using a Donor Plasmid Subjected to Cleavage in the Homologous Region Outside the Cell By electroporation in the gene modification method using the donor polynucleotide shown in Example 2 (1), only the donor plasmid cleaved in advance (10 μg) was introduced to produce the vector-inserted target construct.

inside the cell is not much affected by the length of the homologous region outside the cleavage point, the length of the homologous region outside the designed sequence, and the distance between the cleavage point and the designed sequence; therefore, cleavage in the homologous region inside the cell is thought to be desirable.

Although preferred embodiments of the present invention have been described in detail, it should be obvious to those skilled in the art that these embodiments can be modified. Thus, it is intended that the present invention may be implemented in methods and embodiments other than those described in detail herein. That is, the present invention includes all modifications included in the spirit of the appended "Claims" or the scope sharing the essential part thereof.

INDUSTRIAL APPLICABILITY

The present invention provides novel donor polynucleotides formed by linking the two ends of a genomic fragment comprising a cleavable site by a polynucleotide comprising a positive selection marker gene and a negative selection marker gene. Use of the donor polynucleotide makes it possible to modify only a target gene with avoiding the possibility of introducing mutations to sequences, called "off-target", which are other than the target sequence, by introducing cleavage in a homologous site of the donor polynucleotide without introducing cleavage in a target gene locus. The present invention is a molecular genetic technique for precisely modifying a gene sequence, and is useful

TABLE 6

| Cleavage enzyme | Left arm | Distance between cleavage point and synonymously converted sequence | Right arm | Total cell count | HYG$^R$ | Target inserted constructs | Heterotype or Syn homotype |
|---|---|---|---|---|---|---|---|
| XmaI | 862 | XMAI (1698) Syn | 2910 | 1.6e7 | 3828 | 2 | 0 |
| I-SceI | 1360 | I-SCEI (1200) Syn | 2910 | 8.0e6 | 1228 | 0 | — |
| I-SceI | 1360 | ISCEI (1200) Syn | 2910 | 8.0e6 | 1028 | 0 | — |
| I-SceI | 1960 | ISCEI (600) Syn | 2910 | 8.0e6 | 972 | 0 | 0 |
| Uncut | 2244 | ISCEI (316) Syn | 2910 | 8.0e6 | 2672 | 0 | — |
| Uncut | 2244 | ISCEI (316) Syn | 2910 | 8.0e6 | 2396 | 1 | 0 |
| I-SceI | 2560 | Syn (1200) ISCEI | 1710 | 8.0e6 | 1212 | 2 | 2 |
| I-SceI | 2560 | Syn (1200) ISCEI | 1710 | 8.0e6 | 652 | 0 | — |
| I-SceI | 2560 | Syn (1200) ISCEI | 1710 | 1.6e7 | 2272 | 1 | 1 |

Left arm: length of the homologous region on the left side of the XMAI or ISCEI cleavage site (bp) (see FIG. 1A); length of the homologous region on the left side of the Syn homologously converted sequence site (bp) (see FIG. 2A)
Right arm: length of the homologous region on the right side of the Syn homologously converted sequence site (bp) (see FIG. 1A); length of the homologous region on the right side of the XMAI or ISCEI cleavage site (bp) (see FIG. 2A)

These results confirmed that cleavage in the homologous region of a donor plasmid may take place outside the cell or inside the cell. However, cleavage in the homologous region as a molecular genetic system for precisely modifying a gene sequence for the purpose of gene therapy, breed improvement, and biotechnological creation.

The invention claimed is:

1. An isolated cell comprising:
   1) A circular donor polynucleotide for modifying a genomic sequence of the isolated cell, wherein the circular donor polynucleotide comprises:
      a) a region homologous to the genomic sequence to be modified, wherein the homologous region comprises:
         i) one or more modification positions, wherein each modification position corresponds to a position in the genomic sequence to be modified, and the modification position in the homologous region has a different sequence from the corresponding position in the genomic sequence to be modified; and
         ii) a single cleavable site; and
      b) a linker polynucleotide linking both ends of the homologous region to each other, wherein the linker polynucleotide comprises a positive selection marker gene and a negative selection marker gene; and
   2) A vector that expresses a restriction enzyme capable of cleaving the single cleavable site of the circular donor polynucleotide.

2. The isolated cell of claim 1, wherein the single cleavable site comprises a cleavage sequence.

3. The isolated cell of claim 2, wherein the cleavage sequence is not contained in the genomic sequence of the isolated cell to be modified.

4. The isolated cell of claim 1, wherein in the homologous region, the single cleavable site is positioned upstream or downstream of the one or more modification positions.

5. The isolated cell of claim 1, wherein the linker polynucleotide is a polynucleotide of a plasmid.

6. The isolated cell of claim 1, wherein the circular donor polynucleotide does not comprise a target cell genomic sequence in between the positive selection marker gene and the negative selection marker gene.

7. The isolated cell of claim 1, wherein the positive selection marker gene and the negative selection marker gene are fused, and the positive selection marker and the negative selection marker are expressed as a fusion protein.

8. The isolated cell of claim 1, in which a linearized donor polynucleotide is produced in the isolated cell by cleavage at the single cleavable site of the circular donor polynucleotide by the restriction enzyme.

9. The isolated cell of claim 1, wherein the restriction enzyme is I-SceI or XmaI.

10. The isolated cell of claim 1, wherein the vector is a Sendai virus vector or pCI vector.

* * * * *

SEQUENCE LISTING

<160> NUMBER OF SEQ ID NOS: 42

<210> SEQ ID NO 1
<211> LENGTH: 18
<212> TYPE: DNA
<213> ORGANISM: Artificial sequence
<220> FEATURE:
<223> OTHER INFORMATION: Synthetic Construct

<400> SEQUENCE: 1
tagggataac aggtaat                                                    18

<210> SEQ ID NO 2
<211> LENGTH: 32
<212> TYPE: DNA
<213> ORGANISM: Artificial sequence
<220> FEATURE:
<223> OTHER INFORMATION: Synthetic Construct

<400> SEQUENCE: 2
cttaattaac ctgcagccgg aattgccagc tg                                   32

<210> SEQ ID NO 3
<211> LENGTH: 35
<212> TYPE: DNA
<213> ORGANISM: Artificial sequence
<220> FEATURE:
<223> OTHER INFORMATION: Synthetic Construct

<400> SEQUENCE: 3
atgtggtatg gaattcggtg gccctcctca cgtgc                                35

<210> SEQ ID NO 4
<211> LENGTH: 36
<212> TYPE: DNA
<213> ORGANISM: Artificial sequence
<220> FEATURE:
<223> OTHER INFORMATION: Synthetic Construct

<400> SEQUENCE: 4
tcaccggtca ccatgaaaaa gcctgaactc accgcg                               36

<210> SEQ ID NO 5
<211> LENGTH: 37
<212> TYPE: DNA
<213> ORGANISM: Artificial sequence
<220> FEATURE:
<223> OTHER INFORMATION: Synthetic Construct

<400> SEQUENCE: 5
tcaaaggcag aagcaacttc tacacagcca tcggtcc                              37

<210> SEQ ID NO 6
<211> LENGTH: 36
<212> TYPE: DNA
<213> ORGANISM: Artificial sequence
<220> FEATURE:
<223> OTHER INFORMATION: Synthetic Construct

<400> SEQUENCE: 6
atttaaatca gcggccgcgg atctgcgatc gctccg                               36

<210> SEQ ID NO 7
<211> LENGTH: 32
<212> TYPE: DNA
<213> ORGANISM: Artificial sequence

```
<220> FEATURE:
<223> OTHER INFORMATION: Synthetic Construct

<400> SEQUENCE: 7
tgtctggcca gctagctcag gtttagttgg cc                                    32

<210> SEQ ID NO 8
<211> LENGTH: 25
<212> TYPE: DNA
<213> ORGANISM: Artificial sequence
<220> FEATURE:
<223> OTHER INFORMATION: Synthetic Construct

<400> SEQUENCE: 8
agcctgggca acatagcgag acttc                                            25

<210> SEQ ID NO 9
<211> LENGTH: 28
<212> TYPE: DNA
<213> ORGANISM: Artificial sequence
<220> FEATURE:
<223> OTHER INFORMATION: Synthetic Construct

<400> SEQUENCE: 9
tctggtccct acagagtccc actatacc                                         28

<210> SEQ ID NO 10
<211> LENGTH: 26
<212> TYPE: DNA
<213> ORGANISM: Artificial sequence
<220> FEATURE:
<223> OTHER INFORMATION: Synthetic Construct

<400> SEQUENCE: 10
gctgggatta cacgtgtgaa ccaacc                                           26

<210> SEQ ID NO 11
<211> LENGTH: 26
<212> TYPE: DNA
<213> ORGANISM: Artificial sequence
<220> FEATURE:
<223> OTHER INFORMATION: Synthetic Construct

<400> SEQUENCE: 11
tggctgccca atcacctaca ggattg                                           26

<210> SEQ ID NO 12
<211> LENGTH: 41
<212> TYPE: DNA
<213> ORGANISM: Artificial sequence
<220> FEATURE:
<223> OTHER INFORMATION: Synthetic Construct

<400> SEQUENCE: 12
atccactagt tctagaagcc tgggcaacat agcgagactt c                          41

<210> SEQ ID NO 13
<211> LENGTH: 44
<212> TYPE: DNA
<213> ORGANISM: Artificial sequence
<220> FEATURE:
<223> OTHER INFORMATION: Synthetic Construct

<400> SEQUENCE: 13
caccgcggtg gcggccgctg gctgcccaat cacctacagg attg                       44
```

<210> SEQ ID NO 14
<211> LENGTH: 43
<212> TYPE: DNA
<213> ORGANISM: Artificial sequence
<220> FEATURE:
<223> OTHER INFORMATION: Synthetic Construct

<400> SEQUENCE: 14
tagttctaga gcggccgcag cctgggcaac atagcgagac ttc          43

<210> SEQ ID NO 15
<211> LENGTH: 42
<212> TYPE: DNA
<213> ORGANISM: Artificial sequence
<220> FEATURE:
<223> OTHER INFORMATION: Synthetic Construct

<400> SEQUENCE: 15
attaccctgt tatccctaac ctggttcatc atcactaatc tg           42

<210> SEQ ID NO 16
<211> LENGTH: 44
<212> TYPE: DNA
<213> ORGANISM: Artificial sequence
<220> FEATURE:
<223> OTHER INFORMATION: Synthetic Construct

<400> SEQUENCE: 16
tagggataac agggtaatta tgaccttgat ttatttgca tacc          44

<210> SEQ ID NO 17
<211> LENGTH: 41
<212> TYPE: DNA
<213> ORGANISM: Artificial sequence
<220> FEATURE:
<223> OTHER INFORMATION: Synthetic Construct

<400> SEQUENCE: 17
ggctacgatc tcgacctctt ttgcatacct aatcattatg c            41

<210> SEQ ID NO 18
<211> LENGTH: 21
<212> TYPE: DNA
<213> ORGANISM: Artificial sequence
<220> FEATURE:
<223> OTHER INFORMATION: Synthetic Construct

<400> SEQUENCE: 18
tggttcatca tcactaatct g                                  21

<210> SEQ ID NO 19
<211> LENGTH: 40
<212> TYPE: DNA
<213> ORGANISM: Artificial sequence
<220> FEATURE:
<223> OTHER INFORMATION: Synthetic Construct

<400> SEQUENCE: 19
tagggataac agggtaatat tttgtagaaa cagggttcgc               40

<210> SEQ ID NO 20
<211> LENGTH: 21
<212> TYPE: DNA
<213> ORGANISM: Artificial sequence
<220> FEATURE:
<223> OTHER INFORMATION: Synthetic Construct

```
<400> SEQUENCE: 20
aaaaatatta gctgggagtg g                                             21

<210> SEQ ID NO 21
<211> LENGTH: 20
<212> TYPE: DNA
<213> ORGANISM: Artificial sequence
<220> FEATURE:
<223> OTHER INFORMATION: Synthetic Construct

<400> SEQUENCE: 21
ttgcaagcag cagattacgc                                               20

<210> SEQ ID NO 22
<211> LENGTH: 22
<212> TYPE: DNA
<213> ORGANISM: Artificial sequence
<220> FEATURE:
<223> OTHER INFORMATION: Synthetic Construct

<400> SEQUENCE: 22
gccactgcac ccagccgtat gt                                            22

<210> SEQ ID NO 23
<211> LENGTH: 25
<212> TYPE: DNA
<213> ORGANISM: Artificial sequence
<220> FEATURE:
<223> OTHER INFORMATION: Synthetic Construct

<400> SEQUENCE: 23
ccaggttatg accttgattt atttt                                         25

<210> SEQ ID NO 24
<211> LENGTH: 25
<212> TYPE: DNA
<213> ORGANISM: Artificial sequence
<220> FEATURE:
<223> OTHER INFORMATION: Synthetic Construct

<400> SEQUENCE: 24
ccaggctacg atctcgacct ctttt                                         25

<210> SEQ ID NO 25
<211> LENGTH: 40
<212> TYPE: DNA
<213> ORGANISM: Artificial sequence
<220> FEATURE:
<223> OTHER INFORMATION: Synthetic Construct

<400> SEQUENCE: 25
tagggataac agggtaatca aagcactggg attacaagtg                         40

<210> SEQ ID NO 26
<211> LENGTH: 23
<212> TYPE: DNA
<213> ORGANISM: Artificial sequence
<220> FEATURE:
<223> OTHER INFORMATION: Synthetic Construct

<400> SEQUENCE: 26
ggaggctgag acaggagagt tgc                                           23

<210> SEQ ID NO 27
```

<210> SEQ ID NO 27
<211> LENGTH: 39
<212> TYPE: DNA
<213> ORGANISM: Artificial sequence
<220> FEATURE:
<223> OTHER INFORMATION: Synthetic Construct

<400> SEQUENCE: 27
tagggataac agggtaatca aagtgctggg attacaggc        39

<210> SEQ ID NO 28
<211> LENGTH: 22
<212> TYPE: DNA
<213> ORGANISM: Artificial sequence
<220> FEATURE:
<223> OTHER INFORMATION: Synthetic Construct

<400> SEQUENCE: 28
ggaggccgag gcgggtggat ca        22

<210> SEQ ID NO 29
<211> LENGTH: 39
<212> TYPE: DNA
<213> ORGANISM: Artificial sequence
<220> FEATURE:
<223> OTHER INFORMATION: Synthetic Construct

<400> SEQUENCE: 29
tagggataac agggtaattg tattttagt agagacggg        39

<210> SEQ ID NO 30
<211> LENGTH: 20
<212> TYPE: DNA
<213> ORGANISM: Artificial sequence
<220> FEATURE:
<223> OTHER INFORMATION: Synthetic Construct

<400> SEQUENCE: 30
aaaaaattag ccgggtgtgg        20

<210> SEQ ID NO 31
<211> LENGTH: 44
<212> TYPE: DNA
<213> ORGANISM: Artificial sequence
<220> FEATURE:
<223> OTHER INFORMATION: Synthetic Construct

<400> SEQUENCE: 31
gtcgacccgg gcggccgcca tgataaagc ggaattaatt cccg        44

<210> SEQ ID NO 32
<211> LENGTH: 38
<212> TYPE: DNA
<213> ORGANISM: Artificial sequence
<220> FEATURE:
<223> OTHER INFORMATION: Synthetic Construct

<400> SEQUENCE: 32
ctaaagggaa gcggccgctt attttaaaaa agtttcgg        38

<210> SEQ ID NO 33
<211> LENGTH: 44
<212> TYPE: DNA
<213> ORGANISM: Artificial sequence
<220> FEATURE:
<223> OTHER INFORMATION: Synthetic Construct

<400> SEQUENCE: 33

```
gtcgacccgg gcggccgcca tggataaagc ggaattaatt cccg            44
```

<210> SEQ ID NO 34
<211> LENGTH: 38
<212> TYPE: DNA
<213> ORGANISM: Artificial sequence
<220> FEATURE:
<223> OTHER INFORMATION: Synthetic Construct

<400> SEQUENCE: 34

```
ctaaagggaa gcggccgctt attttaaaaa agtttcgg                   38
```

<210> SEQ ID NO 35
<211> LENGTH: 69
<212> TYPE: DNA
<213> ORGANISM: Artificial sequence
<220> FEATURE:
<223> OTHER INFORMATION: Synthetic Construct

<400> SEQUENCE: 35

```
cgagcctcca agaagaaga gaaaggtcga attgggtacc atgaaaaata ttaagaagaa   60
tcaagtaat                                                          69
```

<210> SEQ ID NO 36
<211> LENGTH: 28
<212> TYPE: DNA
<213> ORGANISM: Artificial sequence
<220> FEATURE:
<223> OTHER INFORMATION: Synthetic Construct

<400> SEQUENCE: 36

```
gttcgggatg gttttcttgt tgttaacg                              28
```

<210> SEQ ID NO 37
<211> LENGTH: 28
<212> TYPE: DNA
<213> ORGANISM: Artificial sequence
<220> FEATURE:
<223> OTHER INFORMATION: Synthetic Construct

<400> SEQUENCE: 37

```
cgttaacaac aagaaaacca tcccgaac                              28
```

<210> SEQ ID NO 38
<211> LENGTH: 69
<212> TYPE: DNA
<213> ORGANISM: Artificial sequence
<220> FEATURE:
<223> OTHER INFORMATION: Synthetic Construct

<400> SEQUENCE: 38

```
atatgcggcc gcgatgaact ttcaccctaa gttttcttta ctacggttat tttaaaaaag   60
tttcggatg                                                          69
```

<210> SEQ ID NO 39
<211> LENGTH: 73
<212> TYPE: DNA
<213> ORGANISM: Artificial sequence
<220> FEATURE:
<223> OTHER INFORMATION: Synthetic Construct

<400> SEQUENCE: 39

```
atatgcggcc gcgacgccac catggataaa gcggaattaa ttcccgagcc tccaaagaag   60
```

```
aagagaaagg tcg                                                          73

<210> SEQ ID NO 40
<211> LENGTH: 830
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (18)..(785)

<400> SEQUENCE: 40
gcggccgcga cgccacc atg gat aaa gcg gaa tta att ccc gag cct cca        50
                   Met Asp Lys Ala Glu Leu Ile Pro Glu Pro Pro
                    1               5                  10 aag aag aag aga aag gtc gaa ttg ggt acc atg aaa aat att aag aag        98
Lys Lys Lys Arg Lys Val Glu Leu Gly Thr Met Lys Asn Ile Lys Lys
            15                  20                  25 aat caa gta atg aat ctg ggt ccg aac tct aaa ctg ctg aaa gaa tac       146
Asn Gln Val Met Asn Leu Gly Pro Asn Ser Lys Leu Leu Lys Glu Tyr
        30                  35                  40 aaa tcc cag ctg atc gaa ctg aac atc gaa cag ttc gaa gca ggt atc       194
Lys Ser Gln Leu Ile Glu Leu Asn Ile Glu Gln Phe Glu Ala Gly Ile
    45                  50                  55 ggt ctg atc ctg ggt gat gct tac atc cgt tct cgt gat gaa ggt aaa       242
Gly Leu Ile Leu Gly Asp Ala Tyr Ile Arg Ser Arg Asp Glu Gly Lys
60                  65                  70                  75 acc tac tgt atg cag ttc gag tgg aaa aac aaa gca tac atg gac cac       290
Thr Tyr Cys Met Gln Phe Glu Trp Lys Asn Lys Ala Tyr Met Asp His
                80                  85                  90 gta tgt ctg ctg tac gat cag tgg gta ctg tcc ccg ccg cac aaa aaa       338
Val Cys Leu Leu Tyr Asp Gln Trp Val Leu Ser Pro Pro His Lys Lys
            95                 100                 105 gaa cgt gtt aac cac ctg ggt aac ctg gta atc acc tgg ggc gcc cag       386
Glu Arg Val Asn His Leu Gly Asn Leu Val Ile Thr Trp Gly Ala Gln
        110                 115                 120 act ttc aaa cac caa gct ttc aac aaa ctg gct aac ctg ttc atc gtt       434
Thr Phe Lys His Gln Ala Phe Asn Lys Leu Ala Asn Leu Phe Ile Val
    125                 130                 135 aac aac aag aaa acc atc ccg aac aac ctg gtt gaa aac tac ctg acc       482
Asn Asn Lys Lys Thr Ile Pro Asn Asn Leu Val Glu Asn Tyr Leu Thr
140                 145                 150                 155 ccg atg tct ctg gca tac tgg ttc atg gat gat ggt ggt aaa tgg gat       530
Pro Met Ser Leu Ala Tyr Trp Phe Met Asp Asp Gly Gly Lys Trp Asp
                160                 165                 170 tac aac aaa aac tct acc aac aaa tcg atc gta ctg aac acc cag tct       578
Tyr Asn Lys Asn Ser Thr Asn Lys Ser Ile Val Leu Asn Thr Gln Ser
            175                 180                 185 ttc act ttc gaa gaa gta gaa tac ctg gtt aag ggt ctg cgt aac aaa       626
Phe Thr Phe Glu Glu Val Glu Tyr Leu Val Lys Gly Leu Arg Asn Lys
        190                 195                 200 ttc caa ctg aac tgt tac gta aaa atc aac aaa aac aaa ccg atc atc       674
Phe Gln Leu Asn Cys Tyr Val Lys Ile Asn Lys Asn Lys Pro Ile Ile
    205                 210                 215 tac atc gat tct atg tct tac ctg atc ttc tac aac ctg atc aaa ccg       722
Tyr Ile Asp Ser Met Ser Tyr Leu Ile Phe Tyr Asn Leu Ile Lys Pro
220                 225                 230                 235 tac ctg atc ccg cag atg atg tac aaa ctg cct aat act att tca tcc       770
Tyr Leu Ile Pro Gln Met Met Tyr Lys Leu Pro Asn Thr Ile Ser Ser
                240                 245                 250
```

-continued

```
gaa act ttt tta aaa taaccgtagt aagaaaaact tagggtgaaa gttcatcgcg      825
Glu Thr Phe Leu Lys
        255 gccgc                                                                830
```

<210> SEQ ID NO 41
<211> LENGTH: 256
<212> TYPE: PRT
<213> ORGANISM: Artificial sequence
<220> FEATURE:
<223> OTHER INFORMATION: Synthetic Construct

<400> SEQUENCE: 41

```
Met Asp Lys Ala Glu Leu Ile Pro Glu Pro Lys Lys Arg Lys
1               5                   10                  15

Val Glu Leu Gly Thr Met Lys Asn Ile Lys Lys Asn Gln Val Met Asn
            20                  25                  30

Leu Gly Pro Asn Ser Lys Leu Leu Lys Glu Tyr Lys Ser Gln Leu Ile
        35                  40                  45

Glu Leu Asn Ile Glu Gln Phe Glu Ala Gly Ile Gly Leu Ile Leu Gly
    50                  55                  60

Asp Ala Tyr Ile Arg Ser Arg Asp Glu Gly Lys Thr Tyr Cys Met Gln
65                  70                  75                  80

Phe Glu Trp Lys Asn Lys Ala Tyr Met Asp His Val Cys Leu Leu Tyr
                85                  90                  95

Asp Gln Trp Val Leu Ser Pro Pro His Lys Lys Glu Arg Val Asn His
            100                 105                 110

Leu Gly Asn Leu Val Ile Thr Trp Gly Ala Gln Thr Phe Lys His Gln
        115                 120                 125

Ala Phe Asn Lys Leu Ala Asn Leu Phe Ile Val Asn Asn Lys Lys Thr
    130                 135                 140

Ile Pro Asn Asn Leu Val Glu Asn Tyr Leu Thr Pro Met Ser Leu Ala
145                 150                 155                 160

Tyr Trp Phe Met Asp Asp Gly Gly Lys Trp Asp Tyr Asn Lys Asn Ser
                165                 170                 175

Thr Asn Lys Ser Ile Val Leu Asn Thr Gln Ser Phe Thr Phe Glu Glu
            180                 185                 190

Val Glu Tyr Leu Val Lys Gly Leu Arg Asn Lys Phe Gln Leu Asn Cys
        195                 200                 205

Tyr Val Lys Ile Asn Lys Asn Lys Pro Ile Ile Tyr Ile Asp Ser Met
    210                 215                 220

Ser Tyr Leu Ile Phe Tyr Asn Leu Ile Lys Pro Tyr Leu Ile Pro Gln
225                 230                 235                 240

Met Met Tyr Lys Leu Pro Asn Thr Ile Ser Ser Glu Thr Phe Leu Lys
                245                 250                 255
```

<210> SEQ ID NO 42
<211> LENGTH: 21
<212> TYPE: PRT
<213> ORGANISM: Artificial sequence
<220> FEATURE:
<223> OTHER INFORMATION: Synthetic Construct

```
<400> SEQUENCE: 42

Met Asp Lys Ala Glu Leu Ile Pro Glu Pro Pro Lys Lys Arg Lys
1               5                   10                  15

Val Glu Leu Gly Thr
            20
```